(12) United States Patent
Cuthbertson et al.

(10) Patent No.: US 6,548,048 B1
(45) Date of Patent: Apr. 15, 2003

(54) LIPOPEPTIDE STABILIZED MICROBUBBLES AS DIAGNOSTIC/THERAPEUTIC AGENTS

(75) Inventors: Alan Cuthbertson, Oslo (NO); Magne Solbakken, Oslo (NO); Henry Raphael Wolfe, Glenmoore, PA (US)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/695,273

(22) Filed: Oct. 25, 2000

Related U.S. Application Data

(63) Continuation of application No. PCT/GB99/01247, filed on Apr. 22, 1999.
(60) Provisional application No. 60/084,833, filed on May 8, 1998.

(30) Foreign Application Priority Data

Apr. 28, 1998 (GB) ............................................. 9809084

(51) Int. Cl.[7] .......................... A61B 8/00; A61K 9/127; A61K 9/14
(52) U.S. Cl. .................... 424/9.52; 424/9.51; 424/450; 424/489; 424/499
(58) Field of Search ............................... 424/9.51, 9.52, 424/9.5, 450, 489, 499; 600/441, 458

(56) References Cited

U.S. PATENT DOCUMENTS

| | | | |
|---|---|---|---|
| 5,228,446 A | | 7/1993 | Unger et al. |
| 5,310,540 A | * | 5/1994 | Giddey et al. ............. 424/9.52 |
| 5,580,575 A | | 12/1996 | Varadarajan et al. |
| 5,670,483 A | | 9/1997 | Zhang et al. |
| 6,231,834 B1 | * | 5/2001 | Unger et al. ................ 424/9.51 |

FOREIGN PATENT DOCUMENTS

| | | |
|---|---|---|
| WO | WO 97 40858 A | 11/1997 |
| WO | WO 98 05364 A | 2/1998 |
| WO | WO 98 18495 A | 5/1998 |
| WO | WO 98 18497 A | 5/1998 |
| WO | WO 98 18498 A | 5/1998 |

OTHER PUBLICATIONS

Caminati G. et al., "Lipopeptides of myelin basic protein in mono–and multilayers", Thin Solid Films, Aug. 31, 1998, XP004151893.

Ono S. et al., "Interaction of Amphipathic Model Lipopeptides with Phospholipid bilayers", Journal of Chromatography, Apr. 24, 1992, XP000676280.

Razafindralambo H. et al., "Foaming Properties of Surfactin, a Lipopeptide Biosurfactant from Bacillus Subtilis", Journal of the American Oil Chemists' Society, Jan. 1, 1996, XP002058919.

Epand R.M., "Biophysical Studies of Lipopeptide–Membrane Interactions", Biopolymers, Jan. 1, 1997, XP000677643.

Maletinska, Lenka et al., "Angiotensin analogues palmitoylated in positions 1 and 4", J. Med. Chem., 1997, XP002116343.

Maletinska, Lenka et al., "168. Lipid masking and reactivation of angiotensin analogues", Helv. Chim. Acta, 1996, XP002116344.

* cited by examiner

*Primary Examiner*—Michael G. Hartley
(74) *Attorney, Agent, or Firm*—Royal N. Ronning, Jr.; Robert F. Chisholm

(57) ABSTRACT

Novel membrane-forming amphiphilic lipopeptides comprising one or more peptide moieties containing 2–50 aminoacyl residues and one or more hydrocarbon chains containing 5–50 carbon atoms. Such lipopeptides may be used in the formation of stabilized gas microbubble dispersions suitable for use as diagnostic and/or therapeutic agents, for example as ultrasound contrast agents.

14 Claims, 3 Drawing Sheets

LIPOPEPTIDE STABILIZED MICROBUBBLES AS DIAGNOSTIC/THERAPEUTIC AGENTS

This application is a continuation of International Application PCT/GB99/01247, filed Apr. 22, 1999, of which the entire disclosure of the pending, prior application is hereby incorporated by reference, which claims benefit of U.S. provisional application No. 60/084,833, filed May 8, 1998, under 35 U.S.C. §119(e).

This invention relates to diagnostic and/or therapeutically active agents comprising gas microbubbles, more particularly to such agents comprising lipopeptide-stabilised gas microbubbles. These agents if desired may incorporate moieties having affinity for sites and/or structures within the body so that diagnostic imaging and/or therapy of particular locations within the body may be enhanced. Of particular interest are diagnostic agents for use in ultrasound imaging. Novel lipopeptides constitute a further feature of the invention.

It is well known that ultrasonic imaging comprises a potentially valuable diagnostic tool, for example in studies of the vascular system, particularly in cardiography, and of tissue microvasculature. A variety of contrast agents have been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas bubbles generated in vivo by intracardiac injection of physiologically acceptable substances have demonstrated the potential efficiency of such bubbles as contrast agents in echography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars, or by entraining or encapsulating the gas or a precursor thereof in a variety of systems, e.g. as porous gas-containing microparticles or as encapsulated gas microbubbles.

There is a substantial body of prior art concerning the nature of encapsulating materials and gases which may be present within microparticles, microbubbles etc. One preferred encapsulating system uses negatively charged phospholidids as wail-forming materials to stabilise gas microbubbles—see WO-A-9729783, which is hereby incorporated by reference and which contains a comprehensive review of prior art in this area. Despite a large amount of research there still remains a need for stabilised gas-filled microbubbles or microparticles which can act as ultrasound contrast agents and which are both physiologically tolerable and echogenic. Many existing contrast agents, for example, are destroyed by continuous ultrasound exposure, and thus any enhancement in contrast agent stability may reduce this problem.

It has recently been found that certain peptides with alternating hydrophobic and hydrophilic residues may spontaneously form macroscopic peptide membranes which may be useful biomaterials for medical products, for example as vehicles for slow-diffusion drug delivery, separation materials, biodegradable polymers and artificial sutures. U.S. Pat. No. 5,670,483 describes membranes formed by the peptide EAK16 derived from the protein zuotin [see also Zhang, S in $Biopolymers$ (1994) 34, 663; Zhang, S in $Biomaterials$ (1995) 16, 1385; and Zhang, S in $Proc. Natl. Acad. Sci$ (1993) 90, 3334]. The membranes are stable in aqueous solutions and are resistant to degradation by heat, enzymatic degradation and alkaline and acidic pH; they have also been found to be non-cytotoxic. These peptides are soluble in aqueous solutions and, according to U.S. Pat. No. 5,670,483, require a sequence length of at least 12 amino acid residues, preferably more than 16 residues, in order to form membrane structures.

Fujita, K. et al. in $Advances in Biophysics$ (1997) 34, 127 have described supramolecular assemblies using helical peptides. When such peptides were suspended in an aqueous medium by a sonication method, a dispersion of vesicles termed "peptosomes" was obtained. These peptosomes had a similar size distribution to classical liposomes, i.e. in the nanometer range; typically their average particle size was 75 nm. Other molecular assemblies comprising peptidic structures have been described by Imanishi, Y. et al. in $Supramol. Sci$ (1996) 13, where gramicidin A/PEG conjugates were found to form peptosomes also in the nanometer size range.

It has now been found that a range of lipid-substituted peptide derivatives, referred to herein as lipopeptides, may be used in the formation of stabilised gas microbubbles suitable for use as diagnostic and/or therapeutic agents, for example in ultrasound echography. Such microbubbles have been found to exhibit good stability, for example during ultrasonication in an imaging procedure. It has also surprisingly been found that lipopetides containing as few as two amino acid residues may exhibit membrane forming properties, in contrast to the findings regarding the self-assembly peptide structures of U.S. Pat. No. 5,670,483. Such short lipopeptides may be prepared relatively easily and economically and may therefore possess substantial cost advantages over naturally occurring, semi-synthetic or synthetic phospholipids such as phosphatidylserine.

Thus according to one aspect of the present invention there is provided a diagnostic and/or therapeutically active agent, e.g. an ultrasound contrast agent, comprising encapsualted gas-filled microbubbles stabilised by membrane-forming amphiphilic lipopeptides.

Viewed from another aspect the invention provides the use of an agent as hereinbefore defined as an ultrasound contrast agent.

Viewed from yet another aspect, the invention provides a method of generating enhanced images of a human or non-human animal body which comprises administering to said body an agent as as hereinbefore defined and generating an ultrasound, magnetic resonance, X-ray, radiographic or light image of at least a part of said body.

The macroscopic membranes may be formed from individual peptide units comprising from 2 to 50 aminoacyl residues. Each peptide unit may carry one or more lipophilic hydrocarbon chains of between 5 and about 50 carbons in length.

In a preferred embodiment the number of amino acid residues in the individual lipopetide units of the invention should be the least number of residues necessary to form an effective stabilised membrane and is preferably less than 20 residues, more preferably less than 10 residues, most preferably between 2 to 8 residues. Clearly, keeping the number of residues to a minimum will both reduce cost and allow easier preparation of the lipopeptides of the invention.

Any amino acid residue may be used in the preparation of individual lipopeptide units according to the invention, although the lipopeptides must be amphiphilic. In a preferred embodiment the lipopeptides will comprise residues of amino acids selected from the readily available naturally occuring essential twenty amino acids.

In one embodiment a peptide unit can comprise alternating hydrophobic and hydrophilic residues, such as alanyl and diaminopropionyl, and may comprise one or more complementary sequences and/or a targeting sequence with affinity for biological receptors. In a particularly preferred embodiment, charged amino acids such as lysine and glutamic acid are selected to provide side-chain functionalities comprising positively and/or negatively charged groups respectively at neutral pH. Although not wishing to be limited by theory, it is envisaged that these charged groups help in the stabilisation of the-outer part of the membrane by forming ion-pairs or salt bridges. The alignment of oppositely charged groups leading to membrane stability is possible only if the peptide sequences involved are complementary to one another and this forms a further aspect of the invention.

The lipid component of the lipopeptides preferably comprises an alkyl, alkenyl or alkynyl chain, especially an alkyl chain. The hydrocarbon chains preferably have between 5 and 25 carbons and most preferably are obtainable from readily available fatty acid derivatives. Suitable fatty acids include oleic acid, stearic acid, palmitic acid and the like; such fatty acids are well-known to the person skilled in the art. The number of hydrocarbon chains per individual lipopetide unit will vary depending on the number of amino acid residues present and will be readily determined by the person skilled in the art; typically each lipopeptide molecule will comprise one or two hydrocarbon chains.

The peptide chains may comprise amino acid sequences that will attain self-stabilising secondary structures such as beta sheets or alpha helices. These may provide the membranes and corresponding microbubbles with advantageous perfomance characteristics such as stability, pharmacokinetics, biotolerability or receptor affinities. A beta sheet-forming lipopeptide, for example such as palmitoyl-(Glu-Ile-Lys-Ile)$_2$, will be stabilised by repeat of counterion and hydrophobicity, and may provide the surface with both ionic and hydrophobic stabilisation.

In addition to the amino acid sequences of the lipopeptides themselves having a stabilising effect, fatty acyl chains linked to amino acid residues in the lipopeptides may be selected to provide the structure with certain characteristics. Thus, for example, mixtures of cis- and trans-unsaturated acyl chains will add to the amorphous nature of the membranes, thereby allowing greater membrane flexibility, especially at higher ultrasound frequencies, e.g. providing better second harmonic signals. A similar increase in amorphous nature or reduction in crystallinity of lipid structures may be obtained by incorporating branched fatty acyl chains, including mixtures of acyl chains with differently located branching.

Alpha helices may be formed in lipopeptides for certain amino acid sequences, as is well known in the art of protein chemistry. In such sequences a number of hydrogen bonds between side chains of properly separated and selected amino acids will serve to keep the peptide chain in alpha helix structures. For example, a structure such as Lys-Lys(acyl)-Gln-Lys(diacyl)-Asn-Lys(acyl)-Gln-Leu will provide strong hydrogen bonding between the Asn and Gln side chains and provide a polar, uncharged surface for microbubbles comprising such structures.

The lipopeptides described above form a further aspect of the invention and may be natural, semisynthetic or synthetic in origin, although the lipopeptides of the invention are preferably produced synthetically. Thus, the invention also provides a membrane-forming amphiphilic peptide of general formula:

A—B (wherein A represents a peptide comprising from 2 to 50 residues and B represents one or more hydrocarbon chains of between 5 and about 50 carbons).

In one embodiment, one or more of the peptide termini or available side-chains may be coupled to a polyethylene glycol derivative in order to delay uptake by the reticuloendothelial system. Polyethylene glycol derivatives are also considered useful in reducing opsonisation of the microbubbles by serum proteins. This is considered especially relevant when targeting of the microbubbles is desirable.

In a further embodiment, multifunctional aromatic systems may be used to link the peptides and lipophilic moieties of the invention to enhance membrane stability. The presence of aromatic systems may further strengthen intermolecular associations within the membrane due to Π-Π stacking interactions. The aromatic group, which may be a carbocyclic or heterocyclic, mono- or polycylic aryl group, is advantageously phenyl. It may link one or more peptides along with one or more hydrophobic hydrocarbon residues. Conveniently, the peptide(s) may be linked to the aromatic system via an amide linkage; for example the N-terminus of a suitable peptide may be coupled to a benzoic acid derivative. One or more hydrophobic groups such as fatty acid derivatives may be linked directly to the aromatic group, for example via an amide linkage, or may be connected to the aromatic group by a suitable linker or linkers. In a preferred embodiment such lipopeptides may be represented by the formula:

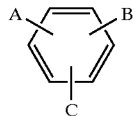

where A is an alkyl chain linked to the phenyl ring by a suitable linker, e.g. an amide group, B is either an alkyl chain linked to the phenyl ring by a suitable linker or a peptide sequence as hereinbefore described linked to the phenyl ring by a suitable linker and C is a peptide sequence as hereinbefore described linked to the phenyl ring by a suitable linker.

Preferably the substituents should be at the 1,3 and 5 positions of the phenyl ring.

A particularly preferred aromatic system is based on 3,5-diaminobenzoic acid. The diaminobenzoic acid scaffold allows for differential coupling without complicated protection strategies being employed. This is due to the reduced reactivity of the second amino group following acylation of the first amino group.

Suitable linking groups for attachment of a hydrocarbon chain or peptide to the aromatic system include amino, hydroxyl, sulfhydryl, carboxyl and carbonyl groups, as well as carbohydrate groups, vicinal diols, thioethers, 2-aminoalcohols, 2-aminothiols, guanidinyl groups, imidazolyl groups, phenolic groups and α-haloacetyl compounds of the type X—CH$_2$CO— (where X=Br, Cl or I). Other linking moieties will of course be readily determined by the person skilled in the art.

The aromatic linked lipopeptides described above form a further aspect of the invention.

In order to form an encapsulating membrane, a homogeneous preparation of a single lipopeptide component or heterogeneous mixtures of two or more complementary lipopeptide components may be used. Preferably a mixture of two complementary lipopeptide components is employed.

The membranes of the microbubbles of the invention may comprise one or more mono-, di- or multi-valent metal ions and, although not wishing to be limited by theory, it is believed that the metal ions may play a role in the stabilisation of the membrane. Suitable metal ions include gadolinium (III), yttrium (III) and calcium (II), but preferably the metal ion will be monovalent, e.g a sodium or potassium ion. The presence of metal ions in the membrane may also facilitate compatibilty with buffering systems and may confer some complexing or chelating stability on the membrane.

In a further embodiment of the invention gas-filled lipopeptide microbubbles incorporating chelates which bind metal ions such as gadolinium, indium or technecium may be prepared. Lipopeptides suitable for iodination, e.g. tyrosine-containing lipopeptides, may form the encapsulating membrane. In this way multi-modality imaging may be carried out.

The microbubble membrane may be a monolayer, bilayer, oligolamellar or a fibrous network of interwoven lipopeptides, for example depending on the method of preparation.

Any biocompatible gas may be present in the microbubbles according to the invention, the term "gas" as used herein including any substances (including mixtures) substantially or completely in gaseous (including vapour) form at the normal human body temperature of 37EC. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane.

Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes and perfluoropentanes, may be particularly advantageous in view of the recognised high stability in the bloodstream of microbubbles containing such gases.

Gas microbubbles preferably have an initial average size not exceeding 10 µm (e.g. of 7 µm or less) in order to permit their free passage through the pulmonary system following administration, e.g. by intravenous injection. However, larger microbubbles may be employed where, for example, these contain a mixture of one or more relatively blood-soluble or otherwise diffusible gases such as air, oxygen, nitrogen or carbon dioxide with one or more substantially insoluble and non-diffusible gases such as perfluorocarbons. Outward diffusion of the soluble/diffusible gas content following administration will cause such microbubbles rapidly to shrink to a size which will be determined by the amount of insoluble/non-diffusible gas present and which may be selected to permit passage of the resulting microbubbles through the lung capillaries of the pulmonary system.

The lipopeptide structures discussed above may advantageously enhance membrane stability by allowing for intermolecular association through a combination hydrophobic, ion-pairing and hydrogen bonding interactions. Hydrogen bonding may occur between donor and acceptor atoms on juxstaposed lipopeptide chains. Hydrophobic interactions may occur between hydrophobic moieties such as alkyl chains or a sequence of hydrophobic amino acid residues, so as to form a hydrophobic inner core of the membrane.

One preferred aspect of this invention relates to the targeting of ultrasound microbubbles for disease imaging and drug delivery. Thus, viewed from another aspect the invention provides a targeted diagnostic and/or therapeutically active agent, e.g. an ultrasound contrast agent, comprising (i) gas-filled microbubbles stabilised by membrane forming amphiphilic lipopeptides capable of interacting with ultrasound irradiation to generate a detectable signal; (ii) one or more vector or drug molecules or a combination of both, where said vector(s) have affinity for a particular target site and/or structures within the body, e.g. for specific cells or areas of pathology; and (iii) one or more linkers connecting said microbubbles and vectors, in the event that these are not directly joined.

The use of vectors to target specific areas of interest within the body is well-known in the art and their use will be routine to the skilled artisan. Suitable vectors of use in the present invention include protein and peptide vectors such as antibodies, cell adhesion molecules such as L-selectin, RGD-peptides, PECAM and intergrin, vectors comprising cytokines/growth factors/peptide hormones and fragments thereof, streptavidin, bacterial fibronectin-binding proteins, Fc-part of antibodies, transferrin, streptokinase/tissue plasminogen activator, plasminogen, plasmin, mast cell proteinases, elastase, lipoprotein, lipase, coagulation enzymes, extracellular superoxide dismutase, heparin cofactor II, retinal survival factor, heparin-binding brain mitogen, apolipoprotein (e.g. apolipoprotein B or apolipoprotein E), adhesion-promoting proteins (e.g. purpurin), viral coat proteins (e.g. from HIV or herpes), microbial adhesins (e.g. β-amyloid precursor), tenascin (e.g. tenascin C), vectors comprising non-peptide agonists/antagonists of cytokines/growth factors/peptide hormones/cell adhesion molecules, vectors comprising anti-angiogenic factors, vectors comprising angiogenic factors, vector molecules other than recognized angiogenetic factors which have known affinity for receptors associated with angiogenesis, receptors/targets associated with angiogenesis, oligonucleotide vectors, modified oligonucleotide vectors, nucleoside and nucleotide vectors, receptors comprising DNA-binding drugs, receptors comprising protease substrates, receptors comprising protease inhibitors, vectors from combinatorial libraries, carbohydrate vectors, lipid vectors and small molecule vectors such as adrenalin and betablockers.

The microbubbles of the invention may be coupled to one or more vectors either directly or through linking groups. The microbubbles may be coupled to vectors such as monoclonal antibodies which recognise specific target areas or to a secondary antibody which has a specificity for a primary antibody which in turn has specificity for a target area. Such use of secondary antibodies is advantageous in that appropriate selection of a secondary antibody allows the preparation of "universal" microbubbles which may be used for a wide range of applications, since the primary antibody can be tailored to particular target areas.

Coupling of a microbubble to a desired vector may be achieved by covalent or non-covalent means for example involving interaction with one or more functional groups located on the microbubble and/or vector. Examples of chemically reactive groups which may be employed for this purpose include amino, hydroxyl, sulfhydryl, carboxyl and carbonyl groups, as well as carbohydrate groups, vicinal diols, thioethers, 2-aminoalcohols, 2-aminothiols, guanidinyl groups, imidazolyl groups and phenolic groups. The vector and microbubble may also be linked by a linking group; many such groups are well-known in the art. Connection of the linker to the vector and microbubble may be achieved using routine synthetic chemical techniques. A comprehensive summary of known vectors and linking groups useful in targeting ultrasonic echography can be found in International Patent Publication No. WO-A-9818501, the contents of which are hereby incorporated by reference.

The present invention also provides a tool for therapeutic drug delivery in combination with vector-mediated direction of the product to the desired site. By "therapeutic drug" is meant an agent having a beneficial effect on a specific disease in a living human or non-human animal. Whilst combinations of drugs and ultrasound contrast agents have been proposed in, for example, WO-A-9428873 and WO-A-9507072, these products lack vectors having affinity for particular sites and thereby show comparatively poor specific retention at desired sites prior to or during drug release.

Therapeutic compounds used in accordance with the present invention may be encapsulated in the interior of the microbubbles or attached to or incorporated in the encapsulating walls. Thus, the therapeutic compound may be linked to a part of the wall, for example through covalent or ionic bonds, or may be physically mixed into the encapsulating material, particularly if the drug has similar polarity or solubility to the membrane material, so as to prevent it from leaking out of the product before its intended action in the body. Release of the drug may be initiated merely by wetting contact with blood following administration or as a consequence of other internal or external influences, e.g. dissolution processes catalyzed by enzymes or the use of of ultrasound. The destruction of gas-containing microparticles using external ultrasound is a well known phenomenon in respect of ultrasound contrast agents, e.g. as described in WO-A-9325241; the rate of release may be varied depending on the type of therapeutic application by using a specific amount of ultrasound energy from the transducer.

The therapeutic agent may be covalently linked to is the encapsulating membrane surface using a suitable linking agent. Thus, for example, one may initially prepare a lipopeptide derivative to which the drug is bonded through a biodegradable or selectively cleavable linker, followed by incorporation of the material into the microbubble. Alternatively, lipidated drug molecules which do not require processing to liberate an active drug may be incorporated directly into the membrane. The active lipidated drug may, for example, be released by increasing the strength of the ultrasound beam.

Exemplary drug delivery systems suitable for use in the present compositions include known therapeutic drugs or active analogues thereof containing thiol groups; these may be coupled to thiol group-containing microbubbles under oxidative conditions yielding disulphide bridges. In combination with a vector or vectors such drug/vector modified microbubbles may be allowed to accumulate in the target tissue; administration of a reducing agent such as reduced glutathione will then liberate drug molecules from the targeted microbubbles in the vicinity of the target tissue, increasing the local concentration of the drug and enhancing its therapeutic effect. It is also possible to prepare microbubbles which may be coupled to or coated with a therapeutic drug immediately prior to use. Thus, for example, a therapeutic drug may be added to a suspension of such microbubbles in an aqueous medium and shaken in order to attach or adhere the drug to the microbubbles.

A comprehensive summary of the use of microbubbles in drug delivery applications can be found in the aforementioned WO-A-9818501.

The lipopeptides of the invention may, for example, be prepared by conventional peptide synthesis techniques using appropriate protection. The synthesis may conveniently be carried out using an automatic peptide synthesiser, for example using the Merrifleld solid phase peptide synthesis technique. Hydrocarbon chains may be coupled to the peptide at any convenient stage, e.g. before a residue has been incorporated into a peptide or after the entire peptide has been synthesised, for example using standard organic chemistry procedures. It is preferred that any hydrocarbon chain carries a carboxylate functionality such as an acyl chloride moiety or carboxylic acid group which may readily be coupled onto a free amino side chain or the N-terminus of the peptide. If the peptide and lipophilic components are to be linked via a aromatic system such as 3,5-diaminobenzoic acid, binding to the aromatic system will be readily effected by the skilled artisan. For example, a peptide may be coupled to the carboxyl acid group of 3,5-diaminobenzoic acid by simple peptide synthesis. A fatty acid may then be coupled to one amino functional groups to yield a 1,3-disubstituted derivative; such reaction with one amino group deactivates the other free amino functionality, so that a 1,3,5-trisubstituted compound does not result. The 1,3-disubstituted derivative may then be coupled further with a desired peptide or lipophilic group, again using simple synthetic chemistry procedures, but using more severe reaction conditions.

Microbubbles according to the invention may, for example, be prepared by sonicating and warming an aqueous solution comprising the required lipopeptide(s) and optionally also any metal ions and/or other desired components, while exposing the solution to an appropriate gas. Other techniques for the preparation of microbubbles, as well as appropriate isolation and purification procedures, are well known in the art.

The invention will now be further described with reference to the following non-limiting examples and the accompanying drawings.

EXAMPLE 1

Figure 1:
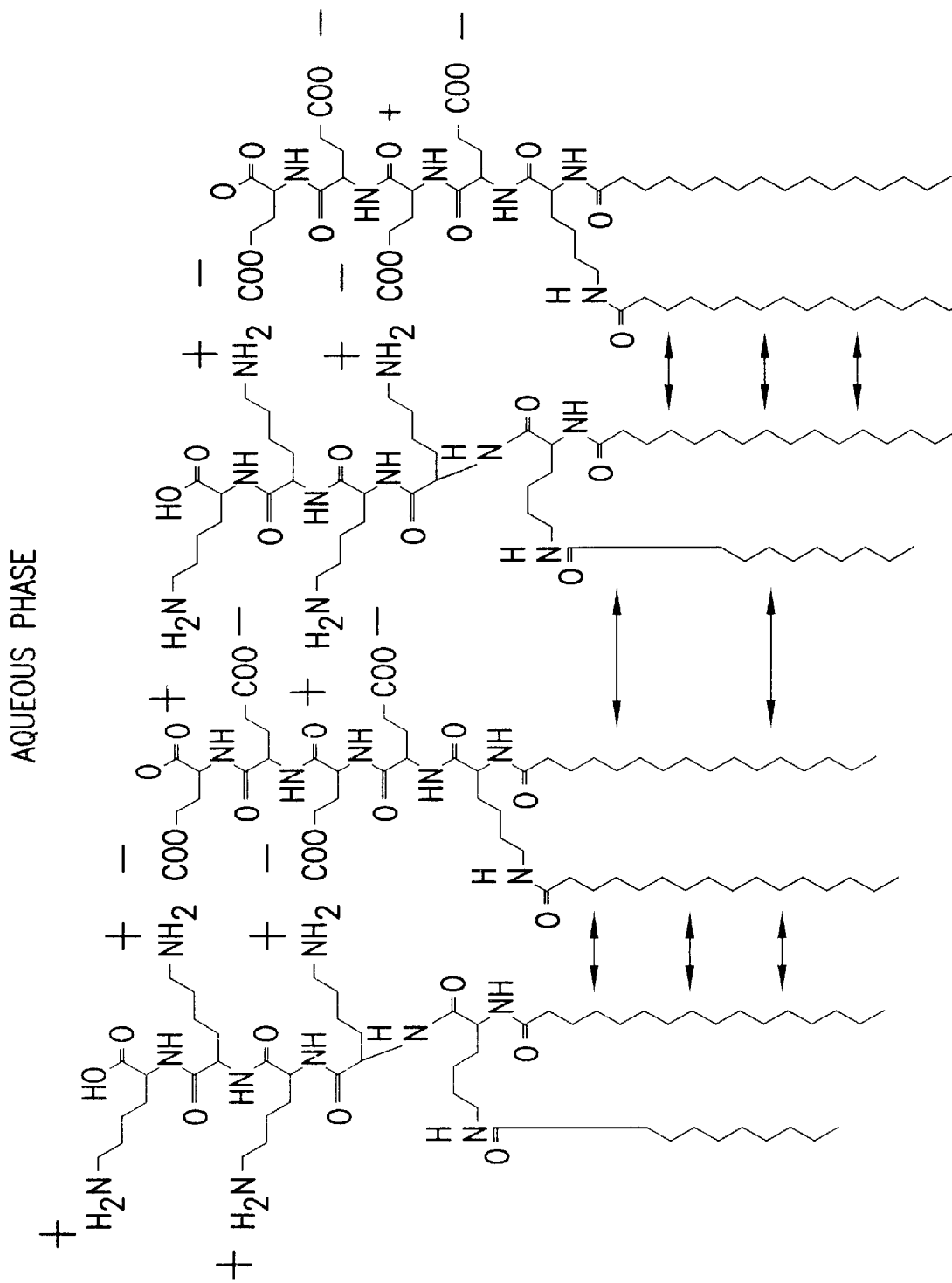
FIG. 1 illustrates the theoretical structure of part of an amphiphilic lipopeptide membrane encapsulating a gas microbubble. The membrane comprises two complementary lipopeptides comprising positively and negatively charged amino acid residues. Hydrophobic interactions are represented by the double-headed arrows.
Figure 2:
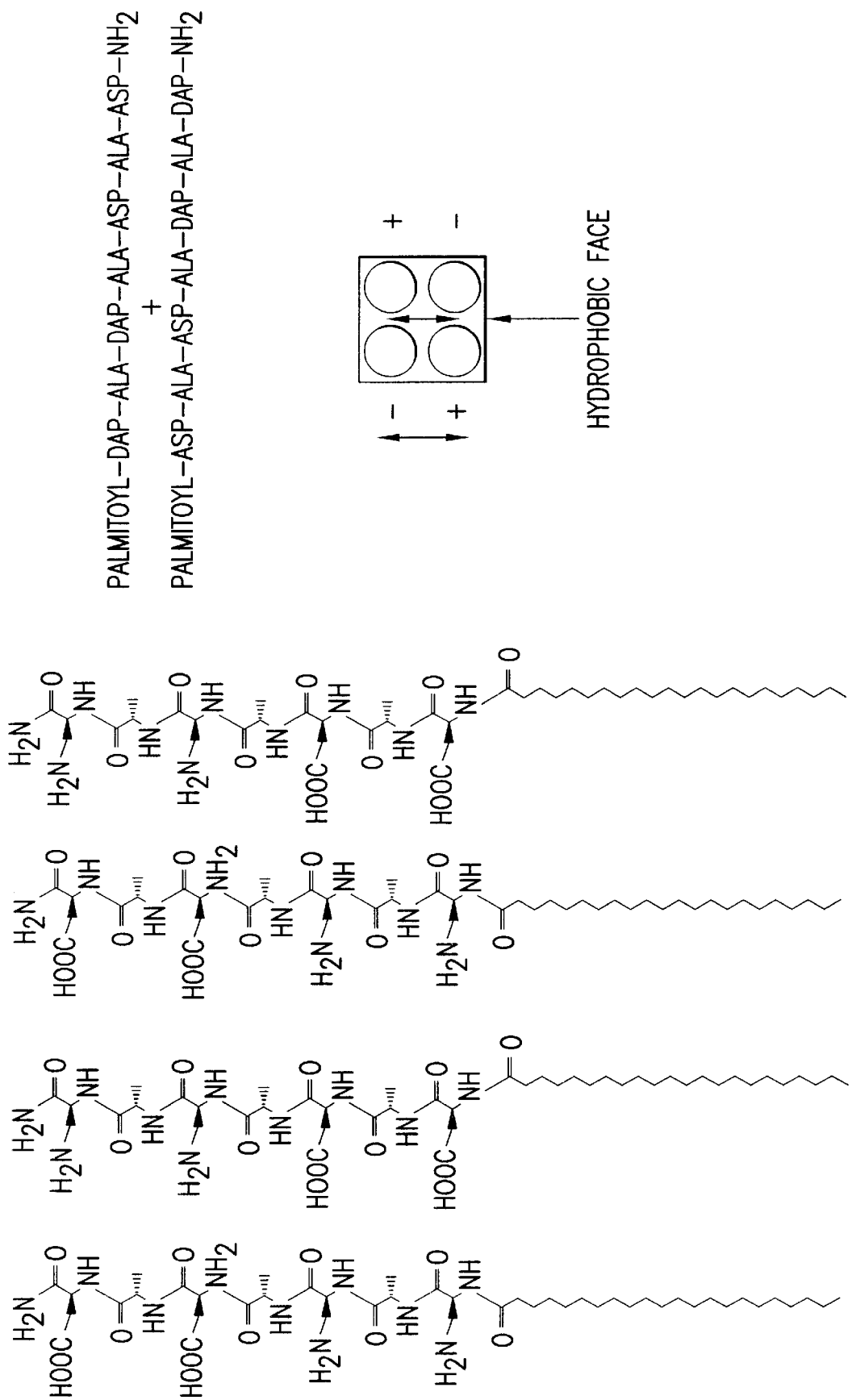
FIG. 2 shows a theoretical representation of a cross-section of gas-containing monolayer membrane comprising a complementary mixture of 2×2 lipopeptides. The top view shows the hydrophobic and ion-pair interactions which are believed to stabilise membrane formation.
Figure 3:
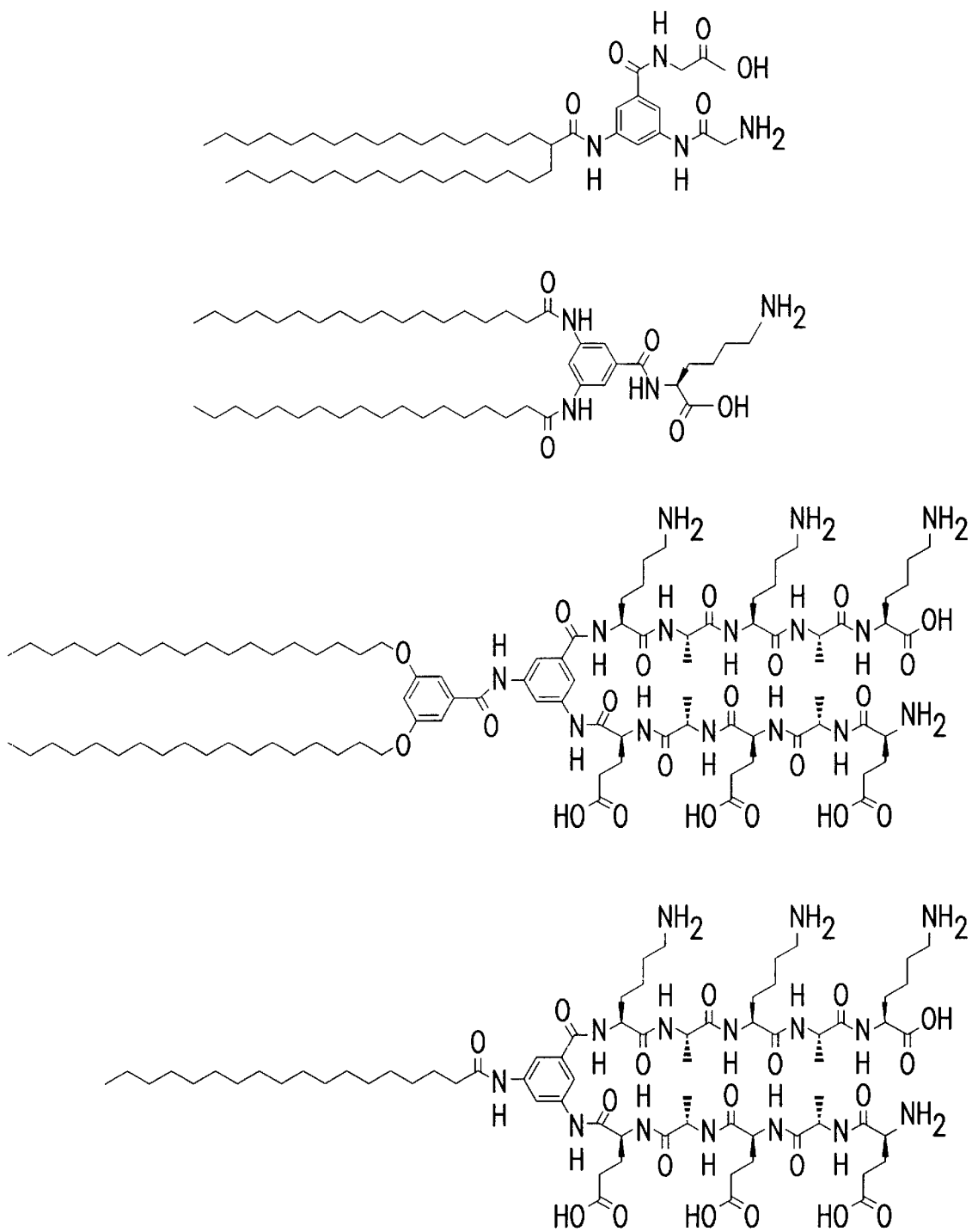
FIG. 3 illustrates the use of 3,5-diaminobenzoic acid as a peptide/lipid linker.

Preparation of Perfluropentane-containing Microbubbles Comprising a 1:1 w/w Mixture of Lipopeptides N-α-palmitoyl-N-ε-palmitoyl-lysinyl-lysinyl-lysinyl-lysinyl-lysine and N-α-palmitoyl-N-ε-palmitoyl-lysinyl-glutamyl-glutamyl-glutamyl-glutamic Acid a) Synthesis of N-α-Palmitoyl-N-ε-palmitoyl-lysinyl-lysinyl-lysinyl-lysinyl-lysine

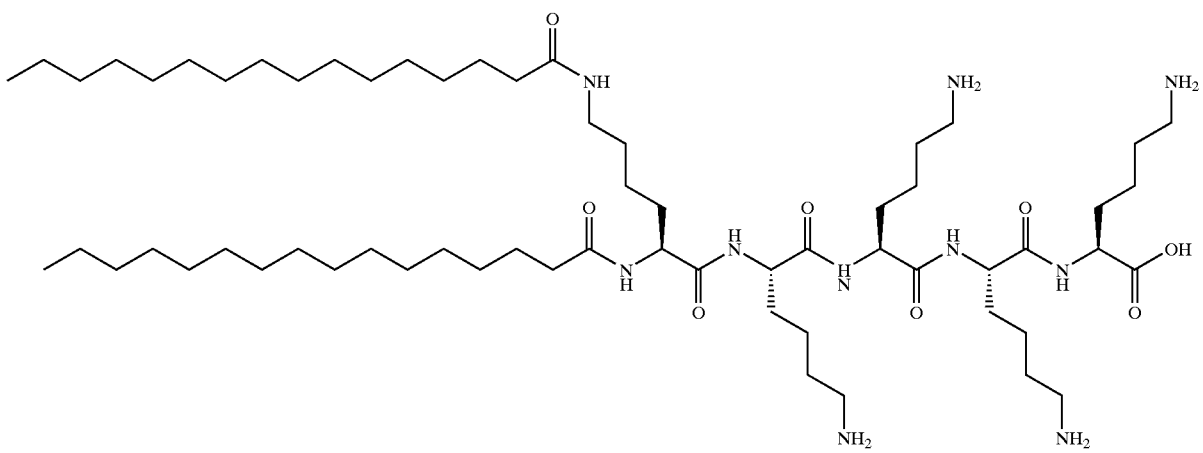

The lipopeptide was synthesised on an ABI 433A automatic peptide synthesiser starting with Fmoc-Lys(Boc)-Wang resin on a 0.25 mmol scale, using 1 mmol amino acid cartridges. All amino acids and palmitic acid were pre-activated with HBTU. Simultaneous removal of peptide from the resin and side-chain protecting groups was carried out in TFA containing 5% $H_2O$ for 2 hours, giving a crude product yield of 200 mg. Purification by preparative HPLC (Vydac 218TP1022 column) of an aliquot of crude material was carried out using a gradient of 80 to 100% B over 40 minutes (A=0.1% TFA/water and B=0.1% TFA/acetonitrile) at a flow rate of 9 ml/min. After lyophilization 65 mg of pure material was obtained (analytical HPLC: gradient 70–100% B where A=0.1% TFA/water and B=0.1% TFA/acetonitrile; column—Vydac 218TP54; detection at UV 214; product retention time=12 minutes). Further product characterization was carried out using MALDI mass spectrometry: expected M+H at 1136, found at 1138.

b) Synthesis of N-α-Palmitoyl-N-ε-palmitoyl-lysinyl-glutamyl-glutamyl-glutamyl-glutamic Acid

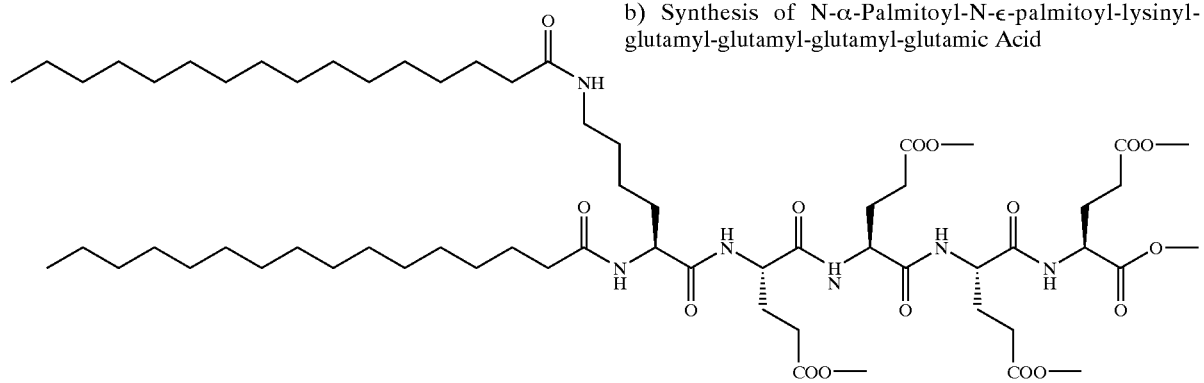

The lipopeptide was synthesised on an ABI 433A automatic peptide synthesiser starting with Fmoc-Glu(OtBu)-Wang resin on a 0.25 mmol scale, using 1 mmol amino acid cartridges. All amino acids and palmitic acid were pre-activated with HBTU. Simultaneous removal of peptide from the resin and side-chain protecting groups was carried out in TFA containing 5% $H_2O$ for 2 hours, giving a crude product yield of 200 mg. Purification on a Sephadex G-200 column using 0.1% ammonia solution gave 30 mg of pure product—detection at UV 214. Product characterization was carried out using MALDI mass spectrometry: expected M+H at 1138, found at 1140.

c) Preparation of Perfluoropentane-containing Microbubbles Comprising a 1:1 w/w Mixture of the Peptides from Example 1(a) and (b)

Stock solution 1: 1.4% propylene glycol/2.4% glycerol in water.

Stock solution 2: 20 mg NaCl dissolved in 10 ml water (ca. 34 mmol).

Stock Solution 3: 4 ml of stock solution 1 was mixed with 1 ml of stock solution 2.

The peptides from Example 1(a) and (b) (1.0 mg of each) were weighed into a clean vial and 0.6 ml of stock solution 3 was added. The mixture was firstly sonicated for 2–3 minutes then warmed to 79° C. and held there for several minutes. The sample was then cooled to room temperature and the head space was flushed with perfluoropentane gas. The vial was shaken in a cap mixer for 60 seconds and the resulting microbubble dispersion was transferred to a clean 5 ml vial. The volume was made up to 4 ml by the addition of water. The scum was allowed to float to the top and the microbubbles were collected from below in a syringe.

d) Characterization of Microbubbles

The semi-fractionated microbubbles of Example 1(c) were analysed by Coulter counter and for pressure stability:

| Size distribution | % |
|---|---|
| Diam. 1–10 micron | 93 |
| Diam. 1–3 micron | 6 |
| Diam. 3–5 micron | 29 |
| Diam. 5–7 micron | 36 |
| Diam. 7–10 micron | 21 |
| Diam. 10–30 micron | 7 |
| Pressure stability | |
| 120 mmHg | stable |
| 160 mmHg | stable |
| 200 mmHg | stable |

EXAMPLE 2

Preparation of Perfluorobutane-containing Microbubbles Comprising N-β-PEG$_{2000}$-Dpr-Lys(Hds)-Lys-Lys(Hds)-Glu-OH (Where Dpr=Diaminopropionic Acid and Hds=2-n-Hexadecylstearic Acid)

a) Synthesis N-β-PEG$_{2000}$-Dpr-Lys(Hds)-Lys-Lys(Hds)-Glu-OH

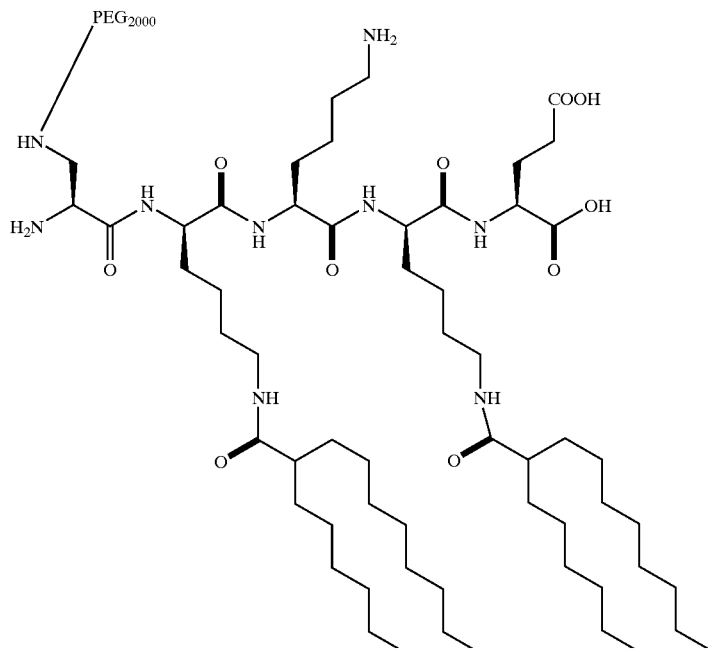

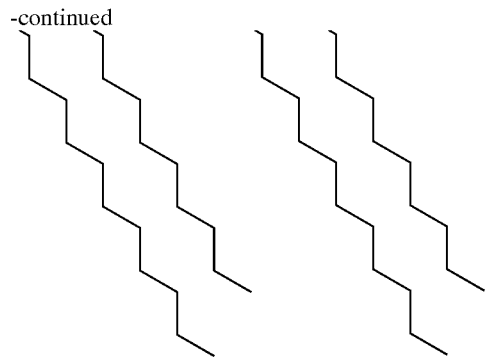

The lipopeptide was synthesised on an ABI 433A automatic peptide synthesiser starting with Fmoc-Glu(OtBu)-Wang resin on a 0.2 mmol scale, using 1 mmol amino acid cartridges. Fmoc-Lys(Dde)—OH was selectively deprotected in 2% hydrazine/DMF solution prior to the coupling of 2-n-hexadecylstearic acid. All amino acids were preactivated with HBTU. Hds and PEG$_{2000}$ were introduced manually following pre-activation with HATU. The simultaneous removal of lipopeptide from the resin and side-chain protecting groups was carried out in TFA containing 5% H$_2$O for 2 hours, giving a crude product yield of 500 mg. Purification by preparative HPLC (Vydac 218TP1022 column-diphenyl) of an aliquot of crude material was carried out using a gradient of 70 to 100% B over 40 minutes (A=water and B=methanol) at a flow rate of 9 ml/minute. After lyophilization 8 mg of pure material was obtained (analytical HPLC: gradient 70–100% B where A=0.1% TFA/water and B=0.1% TFA/acetonitrile; column—Vydac 218TP54; detection at UV 214; product retention time=19.7 minutes). Product characterization was carried out using MALDI mass spectrometry: expected multi M+H peaks around 3600, found 3600.

b) Preparation of Pegylated Lipopeptide Microbubbles 2.5 mg of lipopeptide from Example 2(a) was weighed into a clean vial and 0.5 ml of a solution of 1.4% propylene glycol/2.4% glycerol was added. The mixture was heated to 60° C. for 3 minutes then cooled to room temperature. The head space was flushed with perfluorobutane gas and the vial was shaken in a cap mixer for 30 seconds. The resulting microbubbles were then washed 3 times with deionised water.

c) Characterisation of Microbubbles

The microbubbles suspension of Example 2(b) was analysed for size distribution by Coulter counter:

Diameter 1–3 micron—17.0%
Diameter 3–5 micron—32.4%
Diameter 5–7 micron—25.3%

EXAMPLE 3

Preparation of Perfluoropentane-containing Microbubbles Comprising a Mixture of the Complementary Peptides Palmitoyl-Ala-Glu-Ala-Glu-Ala-Lys-Ala-Lys-Ala-Glu-Ala-Glu-Ala-Lys-Ala-Lys-OH and Palmitoyl-Ala-Lys-Ala-Lys-Ala-Glu-Ala-Glu-Ala-Lys-Ala-Lys-Ala-Glu-Ala-Glu-OH a) Synthesis of Palmitoyl-Ala-Glu-Ala-Glu-Ala-Lys-Ala-Lys-Ala-Glu-Ala-Glu-Ala-Lys-Ala-Lys-OH The lipopeptide was synthesised on an ABI 433A automatic peptide synthesiser starting with Fmoc-Lys(Boc)-Wang resin on a 0.25 mmol scale, using 1 mmol amino acid cartridges. All amino acids and palmitic acid were preactivated with HBTU. Simultaneous removal of peptide from the resin and side-chain protecting groups was carried out in TFA containing 5% H$_2$O for 2 hours, giving a crude product yield of 300 mg. Purification by preparative HPLC (Vydac 218TP1022 column) of a 30 mg aliquot of crude material was carried out using a gradient of 70 to 100% B over 40 minutes (A=water and B=methanol) at a flow rate of 9 ml/minute. After lyophilization 13 mg of pure material was obtained (analytical HPLC: gradient 30–80% B where A=0.1% TFA/water and B=0.1% TFA/acetonitrile; column—Vydac 218TP54; detection at UV 214; product retention time=12.6 minutes). Further product characterization was carried out using MALDI mass spectrometry: expected M+H at 1853, found at 1858.

b) Synthesis of Palmitoyl-Ala-Lys-Ala-Lys-Ala-Glu-Ala-Glu-Ala-Lys-Ala-Lys-Ala-Glu-Ala-Glu-OH The lipopeptide was synthesised on an ABI 433A automatic peptide synthesiser starting with Fmoc-Glu(OtBu)-Wang resin (Novabiochem) on a 0.25 mmol scale, using 1 mmol amino acid cartridges. All amino acids and palmitic acid were preactivated with HBTU. Simultaneous removal of peptide from the resin and side-chain protecting groups was carried out in TFA containing 5% H$_2$O for 2 hours, giving a crude product yield of 300 mg. Purification by preparative HPLC (Vydac 218TP1022 column) of a 30 mg aliquot of crude material was carried out using a gradient of 30 to 80% B over 40 minutes (A=0.1% TFA/water and B=0.1% TFA/acetonitrile) at a flow rate of 9 ml/minute. After lyophilization 4 mg of pure material was obtained (Analytical HPLC: gradient 30–80% B where A=0.1% TFA/water and B=0.1% TFA/acetonitrile; column—Vydac 218TP54; detection at UV 214; product retention time=9.6 minutes). Further product characterization was carried out using MALDI mass spectrometry: expected M+H at 1853, found at 1858.

c) Preparation of Perfluoropentane-containing Microbubbles Comprising a 1:1 w/w Mixture of the Peptides from Example 3(a) and (b)

Stock solution 1: 1.4% propylene glycol/2.4% glycerol in water.

The peptides from Example 3(a) and (b) (0.5 mg of each) were weighed into a clean vial and 0.5 ml of stock solution 1 was added. The mixture was firstly sonicated for 2–3 minutes then warmed to 79° C. and held there for several minutes. The sample was cooled to room temperature and the head space was flushed with perfluoropentane gas. The vial was then shaken in a cap mixer for 120 seconds and the resulting microbubble dispersion was transferred to a clean 5 ml vial. The volume was made up to 4 ml by the addition of water. The scum was allowed to float to the top and the microbubbles were collected from below in a syringe.

d) Characterization of Microbubbles

The semi-fractionated microbubbles of Example 3(c) were analysed for size distribution by Coulter counter:

| Size distribution | % |
| --- | --- |
| Diam. 1–10 micron | 100 |
| Diam. 1–3 micron | 24 |
| Diam. 3–5 micron | 51 |
| Diam. 5–7 micron | 22 |
| Diam. 7–10 micron | 1 |

EXAMPLE 4

Preparation of Perfluorobutane-containing Microbubbles Comprising N-[3-(2-Aminoethanamido)-5-[2-(n-hecadecyl) octadecanamido]-benzoyl]-glycine HPLC: column—Vydac 218TP54; gradient 95 to 100% B over 20 minutes (A and B as above); flow rate 1.0 ml/min; retention time 24.9 minutes detected at 254 nm). Further characterisation was carried out using MALDI mass spectrometry (α-cyano-4-hydroxycinnamic acid matrix), giving m/z for [M+H]$^+$ at 758 as expected.

c) Preparation of Perfluorobutane-containing Microbubbles Comprising N-[3-(2-Aminoethanamido)-5-[2-(n-hecadecyl) octadecanamido]-benzoyl]-glycine DMF (25 μl) was added to a suspension of the compound from Example 4(b) (1 mg) in a solution of 1.4% propylene glycol/2.4% glycerol (0.5 ml). The mixture was heated at 70° C. for 2 minutes and sonicated for 2 minutes. The head space was filled with perfluorobutane and the vial was shaken in a cap mixer for 45 seconds. Microscopy in polarised light showed a pattern characteristic of lamellar type structure around the microbubbles.

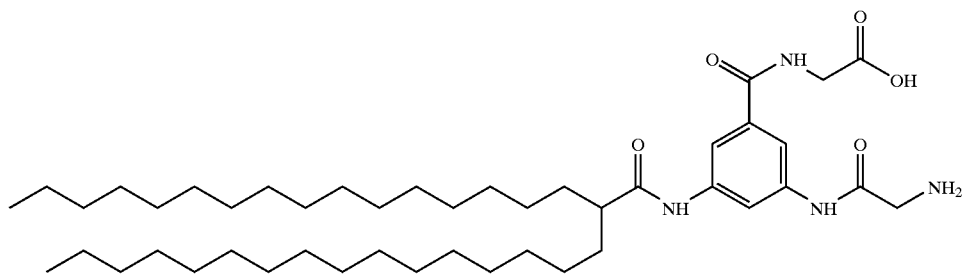

a) Synthesis of 3,5-di(Fmoc-Amino)benzoic Acid

The compound was synthesised from 3,5-diaminobenzoic acid and Fmoc-chloride using sodium bicarbonate as base in a mixture of water and a suitable organic solvent. NMR analytical data were in accordance with the structure.

b) Synthesis of N-[3-(2-Aminoethanamido)-5-[2-(n-hecadecyl)-octadecanamido]benzoyl]glycine The structure was synthesised on a 0.15 mmol scale using a manual nitrogen bubbler apparatus starting with Fmoc-Gly Wang resin and using the compound from example 4(a), 2-n-hexadecylstearic acid and Fmoc-protected glycine. Coupling was carried out using standard TBTU/HOBt/DIEA protocols. Removal of the compound from the resin was carried out using 95% TFA for 2 hours. The product was purified by preparative liquid chromatography (Vydac 218TP1022 column) using a gradient of 90 to 100% B over 60 minutes (A=water/0.1% TFA and B=acetonitrile/0.1% TFA) at a flow rate of 10 ml/minute. After lyophilisation a yield of 4 mg of purified material was obtained (analytical

EXAMPLE 5

Preparation of Perfluorobutane-containing Microbubbles Comprising N$^\alpha$-[3,5-di (Octadecanamido)benzoyl]lysine a) Synthesis of N$^\alpha$-[3,5-di(Octadecanamido)benzoyl]-lysine

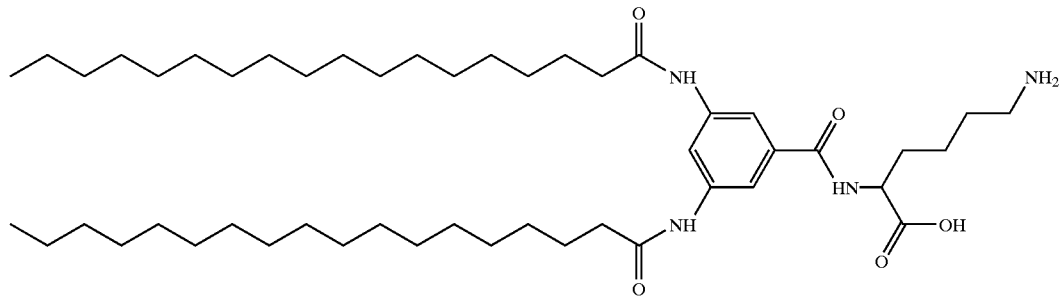

The structure shown was synthesised on a 0.15 mmol scale using a manual nitrogen bubbler apparatus starting with Fmoc-Lys(Boc) Wang resin and using stearic acid and Fmoc-protected 3,5-diaminobenzoic acid from Example 4(a). Coupling was carried out using standard TBTU/HOBt/ DIEA protocols. Simultaneous removal of the compound from the resin and deprotection of the side chain Boc group was carried out using 90% TFA for 3 hours. The product was purified by preparative liquid chromatography (Vydac 218TP1022 column) using a gradient of 90 to 100% B over 60 minutes (A=water/0.1% TFA and B=20% 2-propanol in acetonitrile/0.1% TFA) at a flow rate of 10 ml/minute. After lyophilisation a yield of 46 mg of purified material was obtained (analytical HPLC: column—Vydac 218TP54; gradient 95 to 100% B over 20 minutes (A=water/0.1% TFA and B=acetonitrile/0.1% TFA); flow rate 1.0 ml/minute; retention time 13.2 minutes detected at 254 nm). Further characterisation was carried out using MALDI mass spectrometry (α-cyano-4-hydroxycinnamic acid matrix), giving m/z for [MH]$^+$ at 815, expected 814.

b) Preparation of Perfluorobutane-containing Microbubbles Comprising N$^\alpha$-[3,5-di(Octadecanamido)benzoyl]lysine A mixture of N$^\alpha$-[3,5-di(octadecanamido)benzoyl]lysine (1.4 mg) and a mixture of 1.4% propylene glycol/2.4% glycerol (463 mg) was heated at 60° C. for 2 minutes and then cooled. The head space was then filled with perfluorobutane and the vial was shaken in a cap mixer for 30 seconds. The resulting gas-filled microbubbles were analysed by Coulter counter and for pressure stability.

EXAMPLE 6

Preparation of Lectin-coated Perfluorobutane-containing Lipopeptide Microbubbles for Targeted Ultrasound Imaging a) Synthesis of the Thiol Functionalised Lipid Molecule Palmitoyl-Lys(palmitoyl)-Lys-Lys-Ahx-Cys-OH (Where Ahx=Aminohexanoic Acid)

b) Preparation of Perfluorobutane-containing Microbubbles Comprising a Mixture of Thiol-containing Lipopeptide Structure from Example 6(a) and the Lipopeptide from Example 1(b)

2 mg of the lipopeptide from Example 1(b) and 0.5 mg of the thiol-containing lipopeptide from Example 6(a) were weighed into a clean vial and 0.6 ml of a solution containing 1.4% propylene glycol/2.4% glycerol in 0.05M NaCl was added. The mixture was warmed to 80° C. for 5 minutes. The sample was cooled to room temperature and the head-space flushed with perfluoropropane gas. The vial was shaken in a cap mixer for 60 seconds and the resulting microbubbles were washed once with deionised water.

c) Modification of Lectin with Sulpho-SMPB

To a mixture of 1 mg of fluorescein-labelled lectin (Ulex europaeus, Sigma) in PBS (0.8 ml) was added 0.1 ml DMSO solution containing 1 mg Sulpho-SMPB [sulphosuccinimidyl-4-(p-maleimidophenyl)butyrate—Pierce]. The mixture was stirred for 45 minutes at room temperature then passed through a Sephadex G-200 column using PBS as eluent. The protein fraction was collected and stored at 4° C. prior to use.

d) Microbubble Conjugation with Modified Lectin Protein

To the thiol-containing lipopeptide microbubbles from Example 6(b) was added 1.5 ml of the modified lectin protein solution from Example 6(c). After adjusting the pH of the solution to 8, the conjugation reaction was allowed to proceed for 1 hour at room temperature. The microbubbles were then washed extensively with water.

The lipopeptide structure shown above was synthesized on an ABI 433A automatic peptide synthesiser starting with Fmoc-Cys(Trt)-Wang resin on a 0.25 mmol scale, using 1 mmol amino acid cartridges. All amino acids and palmitic acid were pre-activated using HBTU. Simultaneous removal of peptide from the resin and deprotection of side-chain protecting groups was carried out in TFA containing 5% EDT and 5% water for 2 hours, giving a crude product yield of 250 mg. Purification by preparative HPLC (Vydac 218TP1022 column) of a 40 mg aliquot of crude material was carried out using a gradient of 90 to 100% B over 50 minutes (A=0.1% TFA/water and B=MeOH) at a flow rate of 9 ml/minute. After lyophilization, 24 mg of pure material was obtained (analytical HPLC: gradient 70–100% B where B=0.1% TFA/acetonitrile and A=0.01% TFA/water; column—Vydac 218TP54; detection at UV 214 nm; product retention time=23 minutes). Further product characterization was carried out using MALDI mass spectrometry: expected M+H at 1096, found at 1099.

e) Characterisation of Microbubbles

The microbubble suspension from Example 6(d) was analysed by Coulter counter and for pressure stability:

| Size distribution | |
| --- | --- |
| Diam. 1-10 micron | 84% |
| Diam. 1–3 micron | 12.5% |
| Diam. 3–5 micron | 37% |
| Diam. 1–7 micron | 24% |
| Pressure stability | |
| 120 mmHg | stable |
| 200 mmHg | stable | f) In Vitro Study of Targeted Lectin-coated Perfluorobutane-containing Lipopeptide Microbubbles: Binding to Endothelial Cells Under Flow Conditions The human endothelial cell line ECV 304, derived from a normal umbilical cord (ATCC CRL-1998) was cultured in 260 ml Nunc culture flasks (Chutney 153732) in RPMI 1640 medium (Bio Whittaker) to which L-Glutamine 200 mM, penicillin/streptomycin (10000 U/mL and 10000 mcg/mL) and 10% fetal bovine serum (Hyclone Lot no. AFE 5183) were added. The cells were subcultured with a split ratio of 1:5 to 1:7 when reaching confluence. Cover-glasses, 22 mm in diameter, were sterilised and placed on the bottom of 12 well culture plates before cells in 0.5 ml complete medium with serum were added on top. When the cells reached confluence the coverslips were placed in a custom made flow chamber consisting of a groove carved into a glass plate upon which the coverslip with cells was placed with the cells facing the groove, thereby forming a flow channel. Microbubbles from Example 6(d) were passed from a reservoir held at 37° C. through the flow chamber and back to the reservoir using a peristaltic pump. The flow rate was adjusted to simulate physiologically relevant shear rates. The flow chamber was placed under a microscope and interaction between the microbubbles and cells was viewed directly. A camera mounted on the microscope was connected to a colour video printer and a monitor. A gradual accumulation of the microbubbles on the cells took place, which was dependent on the flow rate. By increasing the flow rate cells started to become detached from the coverslip, with microbubbles still being bound to the cells. Control microbubbles not carrying the vector did not adhere to the endothelial cells and disappeared from the cells under minimal flow conditions.

EXAMPLE 7

Preparation of Perfluorobutane-containing Microbubbles Comprising $N^{\alpha}$-[3,5-di (Octadecanamido)benzoyl]lysine Coated with a FTTC Labelled Lectin for Targeted Ultrasound Imaging a) Preparation of Perfluorobutane-containing Microbubbles Comprising $N^{\alpha}$-[3,5-di(Octadecanamido)benzoyl]lysine Doped with a Thiol-containing Lipopeptide A mixture of 1.4% propylene glycol/2.4% glycerol (1.0 ml) was added to a vial containing thiol-functionalised lipopeptide (0.5 mg) from Example 6(a) and $N^{\alpha}$-[3,5-di (octadecanamido)benzoyl]lysine from Example 5(a) (4.5 mg). The mixture was heated at 60° C. for 3 minutes and then sonicated for 2 minutes, whereafter the head space was filled with perfluorobutane and the vial was shaken in a cap mixer for 45 seconds. The resulting microbubbles were washed with water and large bubbles were removed by simple flotation.

b) Microbubble Conjugation with Modified FITC-labelled Lectin with Sulpho-SMPB

To the microbubble suspension from Example 7(a) was added modified lectin solution from Example 6(c). The reaction was allowed to proceed for 1 hour at room temperature. The microbubbles were washed with deionised water and analysed by Coulter counter (81% between 1 and 3 μm). Presence of lectin was measured by flow cytometry, which indicated a fluorescent population of 75%.

c) Binding to Endothelial Cells

The microbubbles of Example 7(b) were analysed for endothelial cell binding according to the method of Example 6(f).

EXAMPLE 8

Preparation of Charged Lipopeptide Microbubbles Comprising a Mixture of Positively and Negatively Charged Structures a) Synthesis of N-α-Palmitoyl-N-β-palmitoyl-L-diaminopropionoyl-lysinyl-lysine Amide

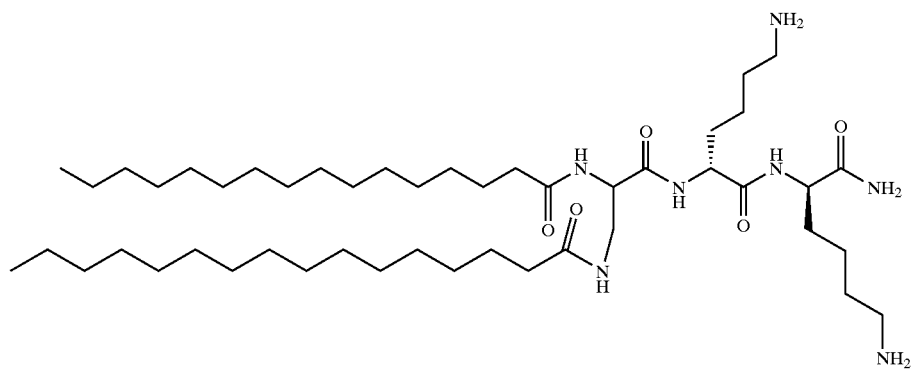

The lipopeptide was synthesised on an ABI 433A automatic peptide synthesiser starting with Rink amide resin on a 0.2 mmol scale, using 1 mmol amino acid cartridges. All amino acids and palmitic acid were pre-activated with HBTU. Simultaneous removal of peptide from the resin and side-chain protecting groups was carried out in TFA containing 5% $H_2O$ for 2 hours, giving a crude product yield of 150 mg. Purification was performed on a Sephadex G-10 gel filtration column using 1:1 methanol/water at pH 2. MALDI mass spectrometry: expected M+H at 836, found at 837. The peptide was dissolved in a 1.4% propylene glycol/2.4% glycerol standard solution at a concentration of 0.5 mg/ml prior to microbubble preparation. The stock solution was adjusted to pH 3 by the addition of 0.1% HCl solution.

b) Synthesis of N-α-Palmitoyl-N-β-palmitoyl-L-diaminopropionoyl-glutamyl-glutamic Acid

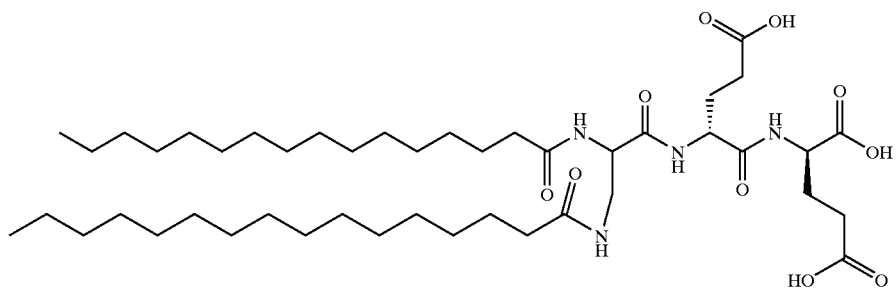

The lipopeptide was synthesised on an ABI 433A automatic peptide synthesiser starting with Fmoc-Glu(OtBu)-Wang resin on a 0.2 mmol scale, using 1 mmol amino acid cartridges. All amino acids and palmitic acid were preactivated with HBTU. Simultaneous removal of peptide from the resin and side-chain protecting groups was carried out in TFA containing 5% $H_2O$ for 2 hours, giving a crude product yield of 120 mg. Purification was performed on a Sephadex G-10 gel filtration column using 1:1 methanol/water at pH 8. MALDI mass spectrometry: expected M+H at 839, found at 839. The peptide was dissolved in a 1.4% propylene glycol/2.4% glycerol standard solution at a concentration of 0.5 mg/ml prior to microbubble preparation. The stock solution was made basic by the dropwise addition of 0.1M NaOH solution to a final pH of 9.

c) Preparation of Microbubbles Using Lipopeptide Mixtures from Example 8(a) and (b)

Different volumes of solutions from Example 8(a) and (b) were mixed together in a vial in order to yield mixtures varying in charge properties. The headspace of the vial was then flushed with perfluoropentane gas and the vial was shaken in a cap mixer for 2 minutes. The resulting microbubbles were then washed several times with distilled water. In a typical experiment where microbubbles with negative Zeta potential were desired, 0.4 ml of the lipopeptide solution from Example 8(b) and 0.2 ml of the lipopeptide solution from Example 8(a) were mixed together in a clean vial and perfluoropentane gas was added to the head space. The vial was placed on the cap mixer and shaken for 2 minutes. The microbubbles were washed several times with distilled water and analysed for pressure stability, size distribution and zeta potential.

EXAMPLE 9

Therapeutic Lipopeptide Microbubble Formulations: Preparation of Doxirubicin-loaded Microbubbles Doxirubicin was dissolved in a 1.4% propylene glycol/2.4% glycerol solution at a concentration of 0.2 mg/ml. To 0.4 ml of the stock solution of negatively charged lipopeptide from Example 8(b) in a clean vial was added 0.2 ml of the stock solution from Example 8(a) and 0.05 ml of the above doxirubicin solution. The resulting solution was an orange-red colour due to the presence of doxirubicin. The head space was then flushed with perfluoropentane gas and the vial was shaken in a cap mixer for 1 minute. Following flotation of the microbubbles it was observed that the orange-red colour was now to be found in the microbubble layer and that the supernatant now contained virtually no colour. The microbubbles were then washed several times with distilled water, following which they still had an orange-red appearance indicating the presence of doxirubicin.

EXAMPLE 10

Therapeutic Lipopeptide Microbubble Formulations: Preparation of Actinomycin D-Loaded Microbubbles The procedure of Example 9 was repeated except that actinomycin D was used in place of doxirubicin. The observed colour was yellow instead of orange-red.

EXAMPLE 11

Preparation of Surface-PEGylated Lipopeptide Microbubbles a) Synthesis of the Lipopeptide: Palmitoyl-Dpr(Palmitoyl)-Arg-Arg-Lys($PEG_{2000}$)—$NH_2$ (Where Dpr=Diaminopropionic Acid)

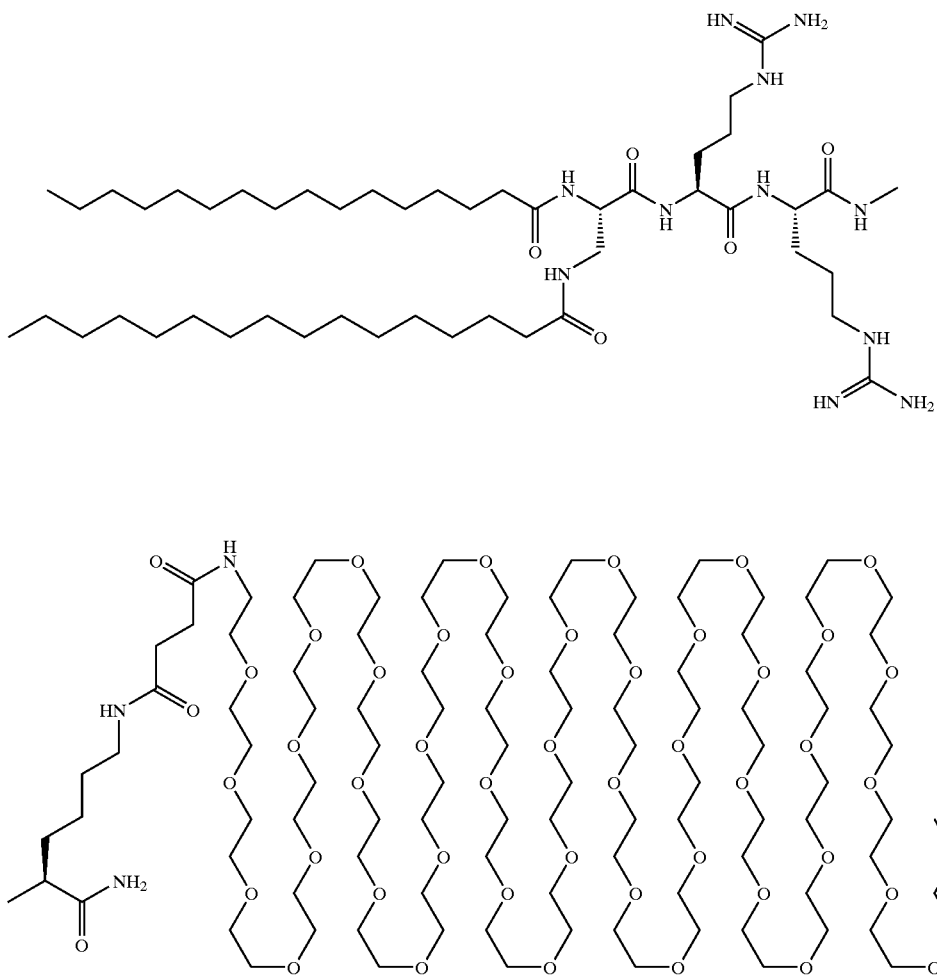

The lipopeptide was partly synthesised on an ABI 433A automatic peptide synthesiser. Starting with Rink amide AM resin (0.25 mmol scale), 1 mmol each of the HBTU activated amino acid derivatives Fmoc-Lys(Dde)OH, Fmoc-Arg(Pmc)—OH, Fmoc-Arg(Pmc)—OH, Fmoc-Dpr(Fmoc)—OH and palmitic acid were assembled on the polymer in the order shown above. The resin was then transferred to a nitrogen bubbler and the Dde protecting group removed by treatment with 2% hydrazine monohydrate in DMF. The $PEG_{2000}$ moiety was then introduced by double coupling with preactivated (HATU) $CH_3O$-POE-$NHCOCH_2CH_2COOH$ (mol mass: 2000 Dalton, Rapp Polymere). Simultaneous removal of peptide and side-chain protecting groups from the resin was carried out in TFA containing 5% phenol, 5% triisopropylsilane and 5% $H_2O$ for 2.5 hours, yielding 27 mg of crude lipopeptide. Product characterisation of the crude lipopeptide was carried out using MALDI mass spectrometry: due to the heterogeneous nature of the $PEG_{2000}$ component a complex spectrum was obtained: $(M+H)^+$ expected range 2900–3200, found 2900–3200. The lipopeptide was dissolved in a 1.4% propylene glycol/2.4% glycerol standard solution at a concentration of 0.5 mg/ml prior to microbubble preparation.

b) Microbubble Preparation

To the lipopeptide solution from Example 8(b) (0.4 ml) in a clean vial was added 0.15 ml of the lipopeptide solution from Example 8(a) and 0.1 ml of the lipopeptide solution from Example 11(a). The head space was then flushed with perfluoropentane gas and the vial was shaken on a cap mixer for 2 minutes to generate perfluoropentane-containing microbubbles. 0.4 ml of distilled water was added to the vial, which was then placed on a roller table for 3 hours. The microbubbles were then washed several times with distilled water and analysed by Coulter counter.

EXAMPLE 12

Preparation of Charged Lipopeptide Microbubbles Comprising a Mixture of Positively and Negatively Charged Structures a) Synthesis of N-α-Palmitoyl-N-β-palmitoyl-L-diaminopropionoyl-lysine

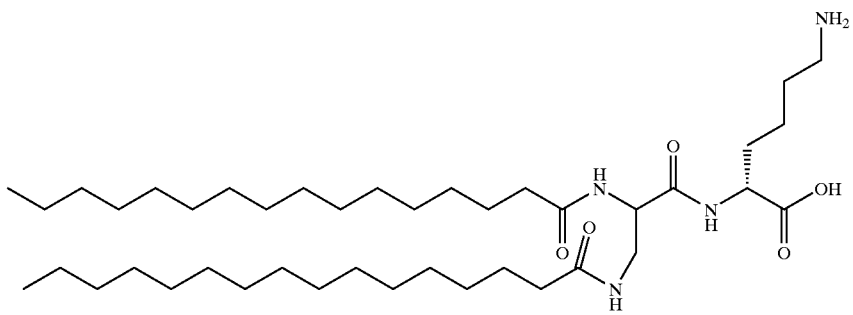

The lipopeptide was synthesised on an ABI 433A automatic peptide synthesiser starting with Fmoc-Lys(Boc)-SASRIN resin on a 0.3 mmol scale, using 1 mmol cartridges and preactivated with HBTU. Simultaneous removal of peptide from the resin and side-chain protecting groups was carried out in TFA containing 5% H$_2$O for 2 hours, giving a crude product yield of 210 mg. MALDI mass spectrometry: expected M+H at 710, found at 709. The lipopeptide was dissolved in a 1.4% propylene glycol/2.4% glycerol standard solution at a concentration of 0.5 mg/ml prior to microbubble preparation. The stock solution was adjusted to pH 2 by the addition of 10% HCl solution.

b) Synthesis of N-α-Palmitoyl-N-β-palmitoyl-L-diaminopropionoyl-glutamic Acid

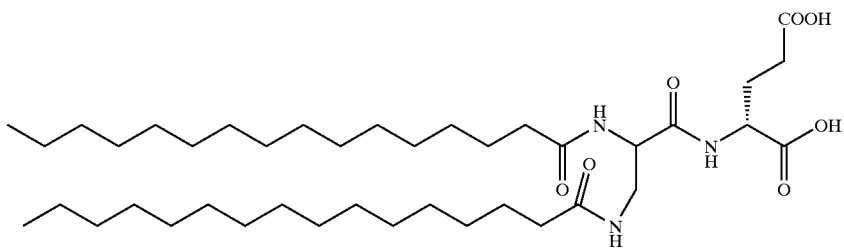

The lipopeptide was synthesised on an ABI 433A automatic peptide synthesiser starting with Fmoc-Glu(OtBu)-Wang resin on a 0.3 mmol scale, using 1 mmol cartridges and HBTU activation. Simultaneous removal of peptide from the resin and side-chain protecting groups was carried out in TFA containing 5% H$_2$O for 2 hours, giving a crude product yield of 150 mg. MALDI mass spectrometry: expected M−H[31] at 709, found at 709. The lipopeptide was dissolved in a 1.4% propylene glycol/2.4% glycerol standard solution at a concentration of 0.5 mg/ml prior to bubble preparation. The solution was made basic by the dropwise addition of 1M NaOH solution to a final pH of 10.

c) Preparation of Microbubbles Using Lipopeptide Mixtures from Example 12(a) and (b) Above To the lipopeptide solution from Example 12(b) (0.4 ml) in a clean vial was added 0.4 ml of the lipopeptide solution from Example 12(a). The head space was then flushed with perfluoropentane gas and the vial was shaken in a cap mixer for 1 minute to generate gas-filled microbubbles. 0.4 ml of distilled water was added to the vial, which was then placed on a roller table for 1 hour. The microbubbles were then washed several times with distilled water and analysed by Coulter counter.

EXAMPLE 13

Synthesis of N-α-Palmitoyl-N-γ-palmitoyl-L-diaminobutyroyl-lysinyl-lysinyl-PEG$_{3400}$-lysinyl-arginyl-lysinyl-arginyl-lysinyl-arginine Amide: a Vector-PEG-lipid Molecule Suitable for Incorporation into Lipopeptide Microbubbles The lipopeptide was synthesised on Rink amide resin on a 0.1 mmol scale, using 1 mmol amino acid cartridges. The vector portion was assembled on an ABI 433 synthesiser using several rounds of Fmoc-Arg(Pmc)—OH followed by Fmoc-Lys(Boc)—OH couplings with HBTU preactivation. To introduce a PEG spacer between the vector and lipid the peptide resin was transferred to a nitrogen bubbler apparatus and Fmoc-PEG$_{3400}$-NHS (Shearwater) coupled to the peptide resin until the Kaiser test was negative. The resin was then transferred back to the synthesiser and the assembly continued with two rounds of Fmoc-Lys(Boc)—OH, one of Di-Fmoc-diaminobutyric acid, and one of palmitic acid to introduce the lipid component. Simultaneous removal of peptide from the resin and side-chain protecting groups was carried out in TFA containing 5% H$_2$O and 5% phenol for 2 hours. The product was purified by reverse phase preparative chromatography (column—Vydac 218TP1022; solvents A=water/0.1% TFA and B=acetonitrile/0.1% TFA; gradient 50–100% B over 40; flow 9 ml/minute; detection at 214 nm) Analytical HPLC of pure product: column—Vydac 218TP54; solvents A=water/0.1% TFA and B=acetonitrile/0.1% TFA; gradient 50–100% B over 20 minutes; flow 1.0 ml/minute; retention time 18.9 minutes detected at 214 nm). Further characterisation was carried out using MALDI mass spectrometry, expected M+H at 4500–5300, found at 4500–5300.

EXAMPLE 14

Synthesis of a Lipopeptide with Positive and Negative Charges Suitable for Microbubble Preparation: Palmitoyl-Dpr(Palmitoyl)-Dpr-Asp-NH$_2$ (Where Dpr=Diaminopropionic Acid)

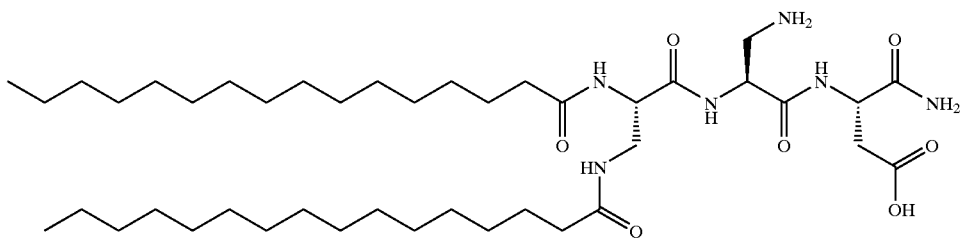

The lipopeptide was synthesised on an ABI 433A automatic peptide synthesiser starting with Rink amide AM resin on a 0.25 mmol scale, using 1 mmol amino acid cartridges. Palmitic acid and the Fmoc amino acid derivatives were preactivated using HBTU before coupling. Simultaneous removal of peptide and side-chain protecting groups from the resin was carried out in TFA (15 ml) containing EDT (0.2 ml) and H$_2$O (0.1 ml) for two hours. Purification of crude material (171 mg) was achieved by recrystallisation from water/methanol (80:20, 20 ml), giving 73 mg of pure material (analytical HPLC: gradient 85–90% B where A=H$_2$O/0.1% TFA and B=CH$_3$CN/0.1% TFA; column—PLRP-S; detection at UV 214 nm; product retention time 17.92 minutes). Further product characterisation was carried out using MALDI mass spectrometry: expected, M+H$^+$ at 782, found at 783).

EXAMPLE 15

Synthesis of a Heparin Sulphate-binding Lipopeptide Suitable for the Preparation of Targeted Lipopeptide Microbubbles: Palmitoyl-Lys(palmitoyl)-Lys-Lys-Ahx-Lys-Arg-Lys-Arg-Lys-Arg-NH$_2$ (Where Ahx=Aminohexanoic Acid)

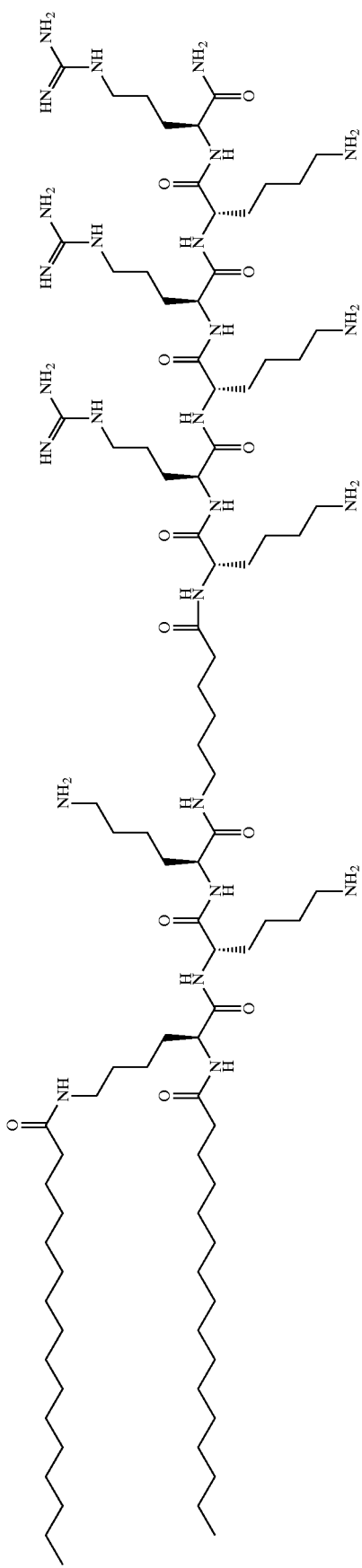

The lipopeptide was synthesized on an ABI 433A automatic peptide synthesiser starting with Rink amide resin (Novabiochem) on a 0.25 mmol scale, using 1 mmol amino acid cartridges. All amino acids and palmitic acid were preactivated using HBTU. Firstly the heparin-binding consensus sequence was assembled using the Fmoc-Arg(Pmc)—OH and Fmoc-Lys(Boc) derivatives. This was followed by introduction of a spacer using Fmoc-aminohexanoic acid and two rounds of Fmoc-Lys(Boc)—OH. Finally the lipid component was introduced by coupling Fmoc-Lys(Fmoc)—OH followed by palmitic acid. Simultaneous removal of peptide and side-chain protecting groups from the resin was carried out in TFA containing 5% phenol, 5% triisopropylsilane and 5% $H_2O$ for 2 hours, giving a crude product yield of 150 mg. Purification by preparative HPLC (Vydac 218TP1022 column) of a 30 mg aliquot of crude material was carried out using a gradient of 70 to 100% B over 40 minutes (A=0.1% TFA/water and B=acetonitrile) at a flow rate of 9 ml/minute. After lyophilization 19 mg of pure material was obtained (analytical HPLC: gradient 70–100% B where B=acetonitrile, A=0.01% TFA/water; column—Vydac 218TP54; detection at UV 214 nm; product retention time=11 minutes). Further product characterization was carried out using MALDI mass spectrometry: expected M+H at 1845, found at 1850.

EXAMPLE 16

Synthesis of the Positively Charged Lipopeptide Palmitoyl-Dpr(palmitoyl)-Arg-Arg-Lys-$NH_2$ Suitable for Lipopeptide Microbubble Preparation (Where Dpr=Diaminopropionic Acid)

The lipopeptide was synthesised on an ABI 433A automatic peptide synthesiser starting with Rink amide resin (Novabiochem) on a 0.25 mmol scale, using 1 mmol amino acid cartridges. All amino acids and palmitic acid were preactivated using HBTU. Simultaneous removal of peptide and side-chain protecting groups from the resin was carried out in TFA containing 5% phenol, 5% triisopropylsilane and 5% $H_2O$ for 2 hours, giving a crude product yield of 50 mg. Purification by preparative HPLC (Vydac 218TP1022 column) of crude material was carried out using a gradient of 90 to 100% B over 40 minutes (A=0.1% TFA/water and B=0.1% TFA/acetonitrile) at a flow rate of 9 ml/minute. After lyophilization 5 mg of pure material was obtained (analytical HPLC: gradient 80–100% B where A=0.1% TFA/water and B=0.1% TFA/acetonitrile; column—Vydac 218TP54; detection at UV 214 nm; product retention time 15 minutes). Further product characterisation was carried out using MALDI mass spectrometry: expected M+H at 1021, found at 1022.

EXAMPLE 17

Synthesis of a Lipopeptide Containing Behenic Acid (Beh)-Beh-Asp-Ala-Asp-Ala-Dpr-Ala-Dpr-NH, Suitable for Use in Microbubble Preparation (Where Dpr=Diaminopropionic Acid)

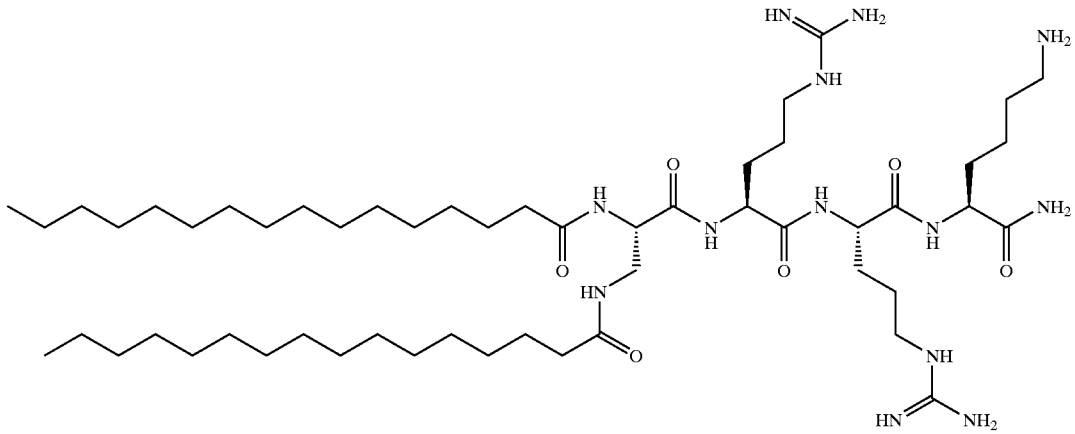

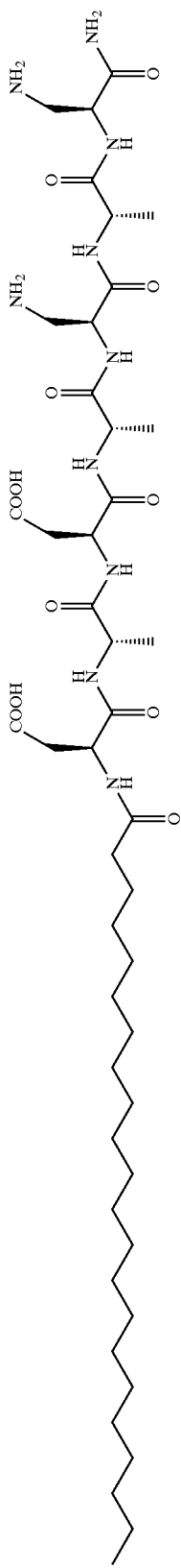

The lipopeptide was synthesised on an ABI 433A automatic peptide synthesiser starting with Rink amide resin (Novabiochem) on a 0.25 mmol scale, using 1 mmol amino acid cartridges. All amino acids and behenic acid were preactivated using HBTU. Simultaneous removal of peptide and side-chain protecting groups from the resin was carried out in TFA containing 5% EDT and 5% $H_2O$ for 2 hours, giving a crude product yield of 150 mg. Purification by preparative HPLC (Vydac 218TP1022 column) of crude material was carried out using a gradient of 70 to 100% B over 40 minutes (A=0.1% TFA/water and B=0.1% TFA/MeOH) at a flow rate of 9 ml/minute. After lyophilization 6 mg of pure material was obtained (analytical HPLC: gradient 70–100% B where A=0.1% TFA/water and B=0.1% TFA/MeOH; column—Vydac 218TP54; detection at UV 214 nm; product retention time 21 minutes). Further product characterisation was carried out using MALDI mass spectrometry: expected M+H at 955, found at 957.

EXAMPLE 18

Preparation of Perfluorobutane-containing Microbubbles Comprising $N^{\alpha}$-[3,5-di (Octadecanamido)benzoyl]lysine with Inclusion of a PEGylated Derivative in the Membrane a) Synthesis of a PEGylated Derivative for Incorporation into the Microbubble Membrane

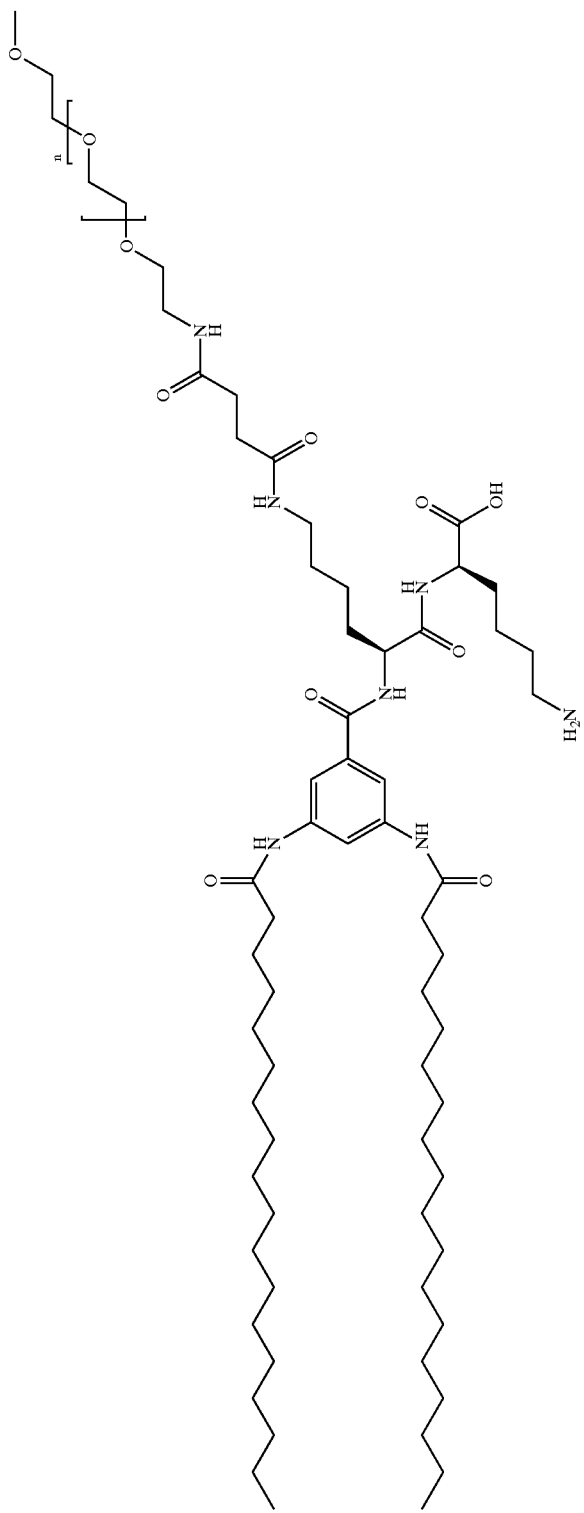

The structure shown was synthesised on a 0.30 mmol scale using a manual nitrogen bubbler apparatus starting with Fmoc-Lys(Boc)-Wang resin. Amino acid, Fmoc-protected 3,5-diaminobenzoic acid from Example 5(a) and stearic acid were preactivated pith TBTU/HOBt/DIEA. The PEGylated side chain was coupled using $CH_3O$-POE-NH—CO—$CH_2CH_2$—COOH (MW 750) from Rapp Polymere. Simultaneous removal of the compound from the resin and deprotection of the side chain Boc group was carried out using 90% TFA for 2.5 hours. The product was purified by reverse phase preparative chromatography (Vydac 218TP1022 column; solvents A=water/0.1% TFA and B=acetonitrile/0.1% TFA; gradient 70–100% B over 60 minutes followed by 100% B for 140 minutes; flow 10 ml/minute; detection at 254 nm). A yield of 83 mg of purified material was obtained (analytical HPLC: column—Vydac 218TP54; solvents: A=water/0.1% TEA and B=acetonitrile/0.1% TFA; gradient 70–100% B over 20 minutes; flow 1.0 ml/minute; retention time 17.4 minutes detected at 254 nm). Further characterisation was carried out using MALDI mass spectrometry (α-cyano-4-hydroxycinnamic acid matrix), giving a distribution of $[M+H]^+$ peaks centred around m/z 1767.

b) Preparation of Perfluorobutane-containing Microbubbles Comprising an 8.5:1 w/w Mixture of $N^\alpha$-[3,5-di(Octadecanamido)benzoyl]lysine and the PEGylated Derivative from Example 18(a)

A mixture of $N^\alpha$-[3,5-di(octadecanamido)benzoyl]lysine from Example 5(a) (1.7 mg), the PEGylated derivative from Example 18(a) (0.2 mg) and a solution of 1.4% propylene glycol/2.4% glycerol (1.0 ml) was heated at 70° C. for 2 minutes to give a homogenous suspension. The head space was filled with perfluorobutane and the vial was shaken in a cap mixer for 60 seconds. Foam was removed and the microbubbles were collected by flotation and washed three times with deionised water.

c) Characterisation of the Microbubbles

The microbubbles from Example 18(b) were analysed by Coulter Multisizer and for pressure stability:

| Size distribution | | |
|---|---|---|
| Diameter (microns) | 1–10 | 99.8% |
| | 1–3 | 84% |
| | 3–5 | 13% |

Acoustic attenuation measurements showed the microbubbles to be stable at overpressures of 120 and 200 mmHg.

The presence of the PEGylated derivative from Example 18(a) in the membrane was confirmed as follows: an aliquot of 100 μl of the microbubble suspension was added to 200 μl of methanol and the mixture was sonicated for 20 seconds. Presence of the derivative from Example 18(a) was shown by analytical HPLC (conditions as described above). Furthermore, the mixture was analysed by MALDI mass spectrometry (α-cyano-4-hydroxycinnamic acid matrix), giving a peak at m/z 814 corresponding to $[M+H]^+$ for $N^\alpha$-[3,5-di(octadecanamido)benzoyl]lysine and a peak distribution centred around m/z 1767 corresponding to the PEGylated derivative.

EXAMPLE 19

Preparation of Perfluorobutane-containing Microbubbles Comprising $N^\alpha$-[3,5-di(Octadecanamido)benzoyl]lysine and a Lipopeptide Containing Captopril for Therapeutic Applications

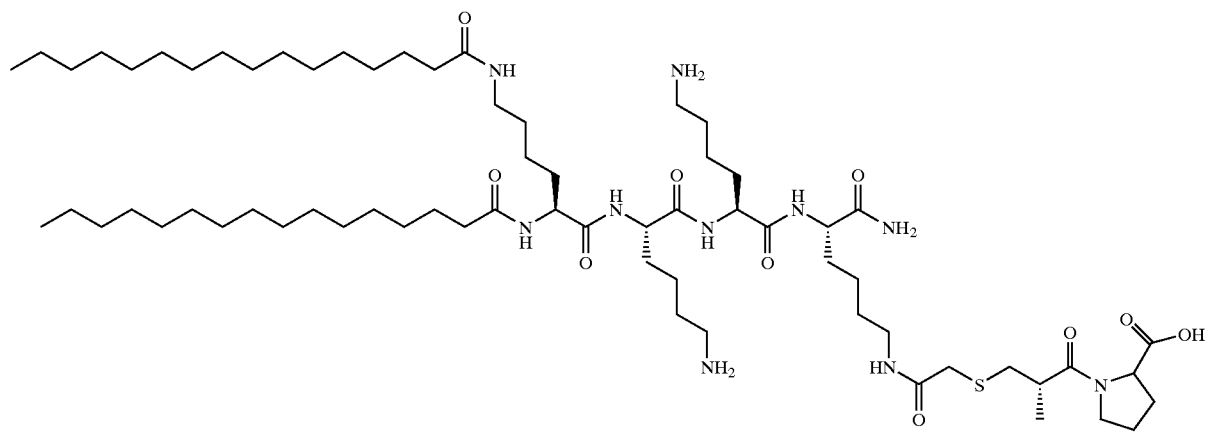

The captopril-containing lipopeptide shown above was synthesised as described in WO-A-9818501. To a vial containing $N^\alpha$-[3,5-di(octadecanamido)benzoyl]]lysine (0.92 mg) and the captopril-containing lipopeptide (0.13 mg) was added a 1.4% propylene glycol/2.4% glycerol mixture (1.0 ml). The vial was heated at 60° C. for 2 minutes and then sonicated to give a homogeneous suspension. The head space was filled with perfluorobutane and the vial was shaken in a cap mixer for 60 seconds. The resulting microbubbles were collected by flotation and washed extensively with deionised water. The microbubbles were analysed by Coulter Multisizer and for pressure stability.

EXAMPLE 20

Preparation of Perfluorobutane-containing Microbubbles Comprising $N^\alpha$-[3,5-di(Octadecanamido)benzoyl]]lysine and a Lipopeptide Containing Atenolol for Diagnostic and Therapeutic Applications

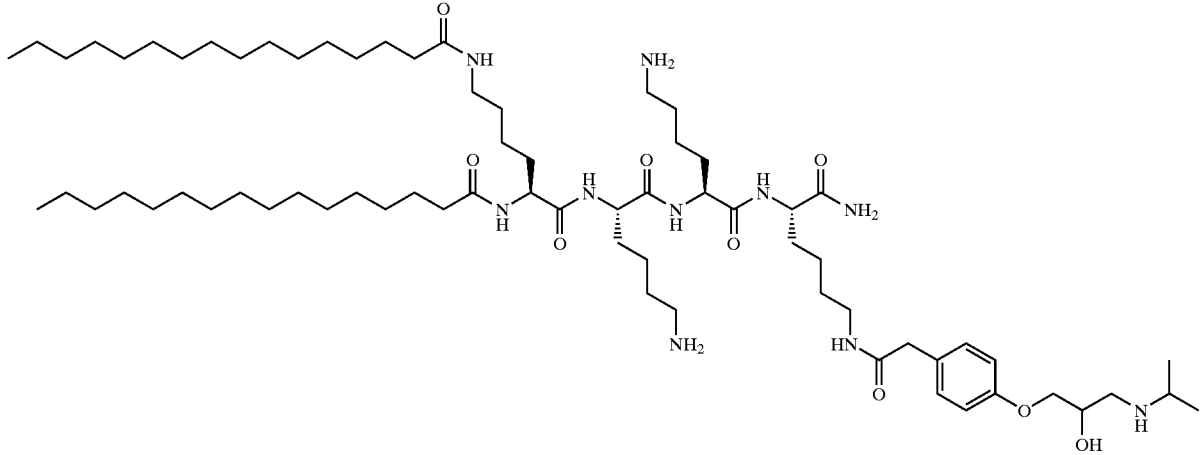

The atenolol-containing lipopeptide shown above was synthesised as described fin WO-A-9818501. Microbubbles were formed according to the procedure described in Example 19, using 0.96 mg of $N^\alpha$-[3,5-di(octadecanamido)benzoyl]]lysine and 0.11 mg of the atenolol-containing lipopeptide. The microbubbles were analysed by Coulter Multisizer and for pressure stability.

EXAMPLE 21

Preparation of Perfluorobutane-containing Microbubbles Comprising $N^\alpha$-[3,5-di(Octadecanamido)benzoyl]]lysine and a Lipopeptide Containing Chlorambucil for Therapeutic Applications

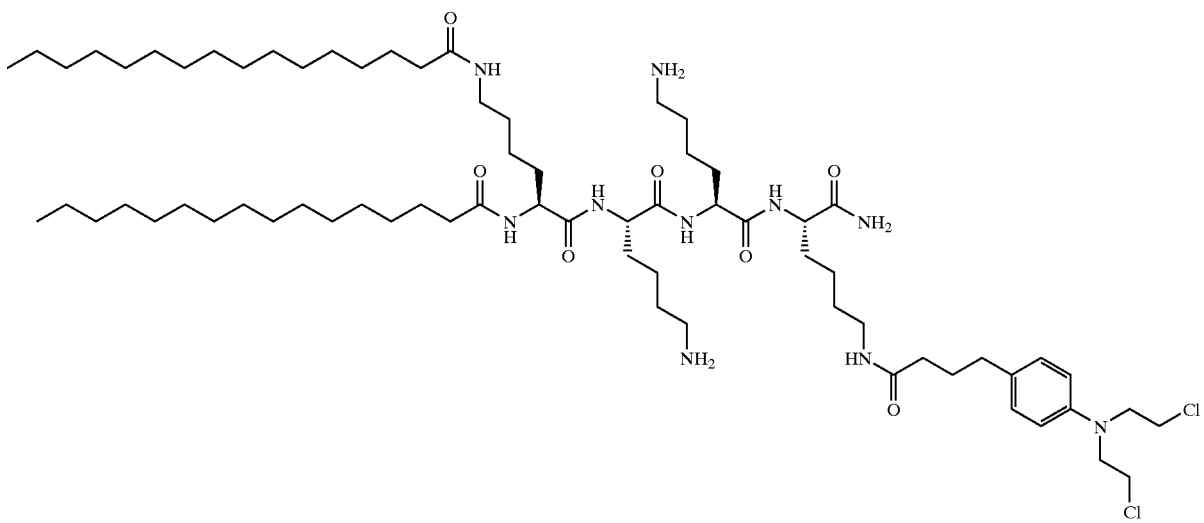

The chlorambucil-containing lipopeptide shown above was synthesised as described in WO-A-9818501. Microbubbles were formed according to the procedure described in Example 19, using 0.97 mg of $N^\alpha$-[3,5-di(octadecanamido)benzoyl]lysine and 0.13 mg of the chlorambucil-containing lipopeptide. The microbubbles were analysed by Coulter Multisizer and for pressure stability.

EXAMPLE 22

Preparation of Perfluorobutane-containing Microbubbles Comprising $N^\alpha$-[3,5-di(Octadecanamido)benzoyl]lysine and a Lipophilic Derivative of Cytarabine for Therapeutic Applications

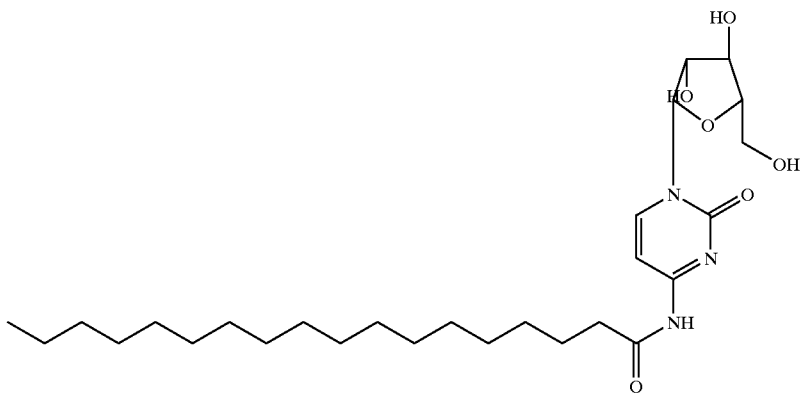

$N^\alpha$-Stearoyl-1-β-D-arabinofuranosylcytosine (structure shown above) was synthesised as described in Akiyama, M. et al. *Chem. Pharm. Bull.* 1978, 26, 981–984. Microbubbles were formed according to the procedure described in Example 19, using 0.97 mg of $N^\alpha$-[3,5-di(octadecanamido)benzoyl]lysine and 0.15 mg of $N^\alpha$-stearoyl-1-β-D-arabinofuranosylcytosine. The microbubbles were analysed by Coulter Multisizer and for pressure stability.

EXAMPLE 23

Synthesis of a Lipopeptide Suitable for Iodination (Multi-modality Imaging): N-α-Palmitoyl-N-ε-palmitoyl-lysinyl-lysinyl-lysinyl-lysinyl-lysinyl-tyrosinyl-tyrosine Amide The lipopeptide was synthesised on an ABI 433A automatic peptide synthesiser starting with Rink amide resin on a 0.2 mmol scale, using 1 mmol amino acid cartridges. All amino acids and palmitic acid were preactivated with HBTU. Simultaneous removal of peptide from the resin and side-chain protecting groups was carried out in TFA containing 5% $H_2O$ and 5% EDT for 2 hours, giving a crude product yield of 300 mg. Purification by preparative HPLC (Vydac 218TP1022 column) of an aliquot of crude material was carried out using a gradient of 50 to 100% B over 40 minutes (A=0.1% TFA/water and B=0.1% TFA/acetonitrile) at a flow rate of 9 ml/minute. After lyophilization 50 mg of pure material was obtained (analytical HPLC: gradient 50–100% B where A=0.1% TFA/water and B=0.1% TFA/acetonitrile; column—Vydac 218TP54; detection at UV 214; product retention time=14 minutes). Further product characterization was carried out using MALDI mass spectrometry: expected M+H at 1463, found at 1462.

What is claimed is:

1. A diagnostic and/or therapeutically active agent comprising encapsulated gas filled microbubbles stabilised by membrane-forming amphiphilic lipopeptides, wherein the peptide moieties of said lipopeptides each comprises less than 20 amino acid residues.

2. A diagnostic agent as claimed in claim 1 which is an ultrasound contrast agent.

3. An agent as claimed in claim 1 wherein said peptide moieties each comprise less than 10 amino acid residues.

4. An agent as claimed in claim 3 wherein said peptide moieties each comprise from 2 to 8 amino acid residues.

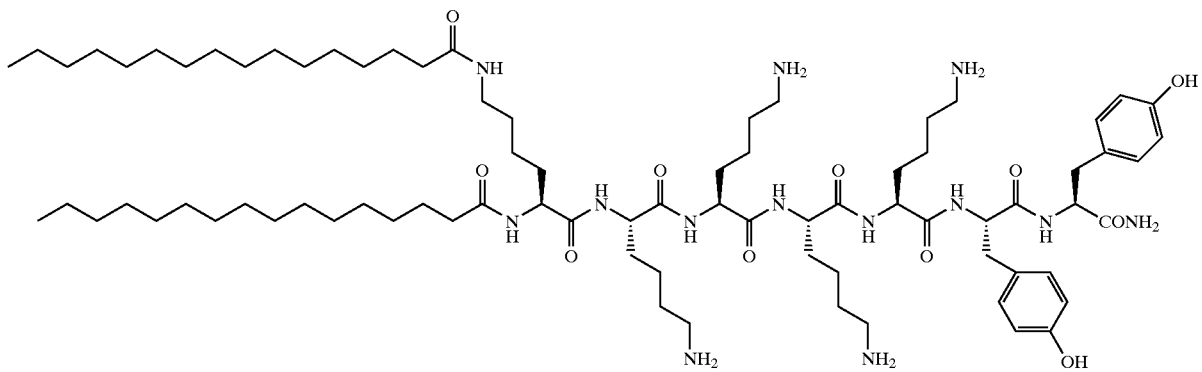

5. An agent as claimed in claim 1 wherein the peptide moieties of said lipopeptides consist of amino acid residues derived from naturally occurring essential amino acids.

6. An agent as claimed in claim 1 wherein the peptide moieties of said lipopeptides comprise alternating hydrophilic and hydrophobic amino acid residues.

7. An agent as claimed in claim 1 wherein the peptide moieties of said lipopeptides are rendered complementary by the presence of oppositely charged groups which are capable of alignment.

8. An agent as claimed in claim 1 wherein the lipid moieties of said lipopeptides comprise alkyl, alkenyl or alkynyl groups containing from 5 to 25 carbon atoms.

9. An agent as claimed in claim 1 wherein the gas comprises air, nitrogen, oxygen, carbon dioxide, hydrogen, an inert gas, a sulphur fluoride, selenium hexafluoride, an optionally halogenated silane, an optionally halogenated low molecular weight hydrocarbon, an ether, a ketone, an ester or a mixture of any of the foregoing.

10. An agent as claimed in claim 9 wherein the gas comprises a perfluorocarbon or a sulphur fluoride.

11. An agent as claimed in claim 10 wherein the gas comprises sulphur hexafluoride, perfluoropropane, perfluorobutane or perfluoropentane.

12. An agent as claimed in claim 1 wherein the lipopeptide has a polyethylene glycol moiety coupled thereto.

13. An agent as claimed in claim 1 further comprising either (a) one or more vectors having affinity for a target site or structure within a human or animal body or (b) a secondary antibody having specificity for a primary antibody which in turn has specificity for such a target site or structure.

14. An agent as claimed in claim 1 further comprising a therapeutic drug.

* * * * *